United States Patent
Minatelli et al.

(10) Patent No.: US 9,763,897 B2
(45) Date of Patent: *Sep. 19, 2017

(54) THERAPEUTIC ASTAXANTHIN AND PHOSPHOLIPID COMPOSITION AND ASSOCIATED METHOD

(71) Applicant: U.S. NUTRACEUTICALS, LLC, Eustis, FL (US)

(72) Inventors: John A. Minatelli, Mount Dora, FL (US); W. Stephen Hill, Ocala, FL (US); Rudi E. Moerck, Sanford, FL (US)

(73) Assignee: U.S. NUTRACEUTICALS, LLC, Eustis, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/658,457

(22) Filed: Mar. 16, 2015

(65) Prior Publication Data

US 2015/0182475 A1    Jul. 2, 2015

Related U.S. Application Data

(60) Continuation-in-part of application No. 14/219,484, filed on Mar. 19, 2014, now abandoned, which is a continuation-in-part of application No. 13/893,572, filed on May 14, 2013, now Pat. No. 8,728,531, which is a division of application No. 13/093,201, filed on Apr. 25, 2011, now Pat. No. 8,663,704.

(60) Provisional application No. 61/329,744, filed on Apr. 30, 2010.

(51) Int. Cl.

| | |
|---|---|
| *A61K 31/122* | (2006.01) |
| *A61K 31/202* | (2006.01) |
| *A61K 9/48* | (2006.01) |
| *A61K 31/685* | (2006.01) |
| *A61K 31/7028* | (2006.01) |
| *A61K 35/612* | (2015.01) |
| *A61K 36/05* | (2006.01) |
| *A61K 36/535* | (2006.01) |
| *A61K 36/537* | (2006.01) |
| *A61K 36/55* | (2006.01) |
| *A61K 45/06* | (2006.01) |
| *A61K 31/66* | (2006.01) |
| *A61K 35/60* | (2006.01) |
| *A23P 10/30* | (2016.01) |
| *A23L 33/105* | (2016.01) |
| *A23L 33/115* | (2016.01) |

(52) U.S. Cl.
CPC .......... *A61K 31/122* (2013.01); *A23L 33/105* (2016.08); *A23L 33/115* (2016.08); *A23P 10/30* (2016.08); *A61K 9/48* (2013.01); *A61K 9/4858* (2013.01); *A61K 31/202* (2013.01); *A61K 31/66* (2013.01); *A61K 31/685* (2013.01); *A61K 31/7028* (2013.01); *A61K 35/60* (2013.01); *A61K 35/612* (2013.01); *A61K 36/05* (2013.01); *A61K 36/535* (2013.01); *A61K 36/537* (2013.01); *A61K 36/55* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 8,030,037 B2 | 10/2011 | Thomas et al. | |
| 8,030,348 B2 | 10/2011 | Sampalis | |
| 8,481,072 B2 | 7/2013 | Minatelli et al. | |
| 8,524,980 B2 | 9/2013 | Minatelli | |
| 8,663,704 B2 | 3/2014 | Minatelli et al. | |
| 8,728,531 B2 | 5/2014 | Minatelli | |
| 8,784,904 B2 | 7/2014 | Minatelli et al. | |
| 8,945,608 B2 | 2/2015 | Minatelli | |
| 8,962,924 B2 | 2/2015 | Minatelli | |
| 9,138,452 B2 | 9/2015 | Minatelli | |
| 9,192,671 B2 | 11/2015 | Minatelli | |
| 9,295,698 B2 | 3/2016 | Minatelli | |
| 9,295,699 B2 | 3/2016 | Minatelli | |
| 9,351,982 B2 | 5/2016 | Minatelli | |
| 2003/0091652 A1 | 5/2003 | Ishaq | |
| 2003/0096794 A1 | 5/2003 | Niehoff | |

(Continued)

FOREIGN PATENT DOCUMENTS

| | | |
|---|---|---|
| CN | 102746947 | 10/2012 |
| EP | 1 417 211 | 5/2007 |

(Continued)

OTHER PUBLICATIONS

Nuno et al., "Effects of the Marine Microalgae Isochrysis Galbana and Nannochloropsis Oculata in Diabetic Rats," Journal of Functional Foods, vol. 5, No. 1, Jan. 2013, pp. 106-115.

Hurst et al., "Dietary Fatty Acids and Arthritis," Prostaglandins, Leukotrienes and Essential Fatty Acids, vol. 82, No. 4-6, Apr. 1, 2010, pp. 315-318.

Ierna et al., "Supplementation of Diet With Krill Oil Protects Against Experimental Rheumatoid Arthritis," BMC Musculoskeletal Disorders, Biomed Central Ltd., vol. 11, No. 1, Jun. 29, 2010, 11 pages.

(Continued)

*Primary Examiner* — Michelle F Paguio Frising
(74) *Attorney, Agent, or Firm* — Allen, Dyer, Doppelt & Gilchrist, P.A.

(57) ABSTRACT

A dietary supplement includes comprising a therapeutic amount of astaxanthin derived from a synthetic or natural ester or diol, and at least one of a phospholipid, glycolipid, and sphingolipid, and formulated into an oral dosage form, wherein the astaxanthin is 0.1 to 15 percent by weight of the at least one phospholipid, glycolipid, and sphingolipid. The composition includes 0.5 to 12 mg of astaxanthin and may be used to treat low density lipoprotein (LDL) oxidation in humans and other diseases, disorders and impairments.

10 Claims, No Drawings

(56) References Cited

U.S. PATENT DOCUMENTS

| | | |
|---|---|---|
| 2004/0180851 A1 | 9/2004 | Long et al. |
| 2004/0234587 A1 | 11/2004 | Sampalis |
| 2004/0241249 A1 | 12/2004 | Sampalis |
| 2006/0217445 A1 | 9/2006 | Chew |
| 2006/0265766 A1* | 11/2006 | Kyle ..................... A01K 61/00 800/13 |
| 2007/0098808 A1 | 5/2007 | Sampalis |
| 2007/0122452 A1 | 5/2007 | Moriguchi et al. |
| 2008/0014282 A1 | 1/2008 | Long et al. |
| 2008/0166779 A1 | 7/2008 | Thomas et al. |
| 2008/0274203 A1 | 11/2008 | Bruheim et al. |
| 2009/0061067 A1 | 3/2009 | Tilseth et al. |
| 2009/0170808 A1 | 7/2009 | Ling et al. |
| 2009/0181114 A1 | 7/2009 | Minatelli et al. |
| 2009/0181127 A1 | 7/2009 | Minatelli et al. |
| 2009/0258081 A1 | 10/2009 | Minatelli et al. |
| 2010/0291053 A1 | 11/2010 | Clayton et al. |
| 2011/0117207 A1 | 5/2011 | Minatelli et al. |
| 2011/0160161 A1 | 6/2011 | Sampalis et al. |
| 2011/0195061 A1 | 8/2011 | Minatelli et al. |
| 2011/0268811 A1 | 11/2011 | Minatelli et al. |
| 2012/0088011 A1 | 4/2012 | Thomas et al. |
| 2013/0059768 A1 | 3/2013 | Hallaraker et al. |
| 2014/0205627 A1 | 7/2014 | Minatelli et al. |

FOREIGN PATENT DOCUMENTS

| | | |
|---|---|---|
| FR | 2835703 | 8/2003 |
| GB | 2 103 088 | 2/1983 |
| WO | 02/090560 | 11/2002 |
| WO | 03/011873 | 2/2003 |
| WO | 2004112776 | 12/2004 |
| WO | 2005/037848 | 4/2005 |
| WO | 2011050474 | 5/2011 |
| WO | 2013/032333 | 3/2013 |
| WO | 2014/013335 | 1/2014 |
| WO | 2014/014766 | 1/2014 |

OTHER PUBLICATIONS

Ruff et al., "Eggshell Membrane: A Possible New Natural Therapeutic for Joint and Connective Tissue Disorders, Results from Two Open-Label Human Clinical Studies," Clinical Interventions in Aging 2009; vol. 4, May 2009, pp. 235-240.

Ruff et al., "Eggshell Membrane in the Treatment of Pain and Stiffness from Osteoarthritis of the Knee: A Randomized, Multicenter, Double-blind, Placebo Controlled Clinical Study," Clinical Rheumatology; Journal of the International League of Associations for Rheumatology; vol. 28, No. 8; Apr. 2009; pp. 907-914.

Kamath et al., "Ulcer preventive and antioxidative properties of astaxanthin from Haematococcus pluvialis", European Journal of Pharmacology 2008, vol. 590, pp. 387-395.

Mercola, "Astaxanthin for Heart Health and Chronic Pain," Downloaded from the Internet on Dec. 4, 2013 at www.mercola.com, Sep. 12, 2012, pp. 1-6.

Breithaupt, "Identification and Quantification of Astaxanthin Esters in Shrimp (*Pandatus borealis*) and in a Microalga (*Haematococcus pluvialis*) by Liquid Chromatography-Mass Spectrometry Using Negative Ion Atmospheric Pressure Chemical Ionization," Institut fur Lebensmittelchernie, Universitat Hohenheim, Germany, Apr. 14, 2004, pp. 1-6.

Yamaguchi et al., "Supercritical Carbon Dioxide Extraction of Oils from Antarctic Krill," J. Agric. Food Chem., vol. 34, No. 5, American Chemistry Society, 1986, pp. 904-907.

Lyberg et al., "Enzymatic and Chemical Synthesis of Phosphatidylcholine Regioisorners Containing Eicosapentaenoic Acid or Docosahexaenoic Acid," European Journal of Lipid Science and Technology, vol. 107, No. 5, May 1, 2005, pp. 279-290.

Kim et al., "Phospholipase A1-Catalyzed Synthesis of Phospholipids Enriched in n-3 Polyunsaturated Fatty Acid Residues," Enzyme and Microbial Technology, vol. 40, No. 5, Mar. 8, 2007, pp. 1130-1135.

Gbogouri et al., "Analysis of Lipids Extracted from Salmon (*Salmo saler*) Heads by Commercial Proteolytic Enzymes," European Journal of Lipid Science and Technology, vol. 108, No. 9, Sep. 1, 2006, pp. 766-775.

Linder et al., "Proteolytic Extraction of Salmon Oil and PUFA Concentration by Lipases," Marine Biotechnology, vol. 7, No. 1, Feb. 1, 2005, pp. 70-76.

Peng et al., "Polyunsaturated Fatty Acid Profiles of Whole Body Phospholipids and Triacylglycerols in Anadromous and Landlocked Atlantic Salmon (*Salmo salar* L.) Fry," Comparative Biochemistry and Physiology Part B: Biochemistry and Molecular Biology, vol. 134, No. 2, Feb. 1, 2003, pp. 335-348.

Wjendran et al., "Efficacy of Dietary Arachidonic Acid Provided as Triglyceride or Phospholipid as Substrates for Brain Arachidonic Acid Accretion in Baboon Neonates," Pediatric Research, vol. 51, No. 3, Mar. 1, 2002, pp. 265-272.

Kidd, "Omega-3 DHA and EPA for Cognition, Behavior, and Mood: Clinical Findings and Structural-Functional Synergies with Cell Membrane Phospholipids," Alternative Medicine Review, vol. 12, No. 3, Sep. 2007, pp. 207-227.

Linder et al., "Response Surface Optimisation of Lipase-Catalysed Esterification of Glycerol and n-3 Polyunsaturated Fatty Acids From Salmon Oil," Process Biochemistry, vol. 40, No. 1, Jan. 1, 2005, pp. 273-279.

Longvah et al., "Nutritional and Short Term Toxicological Evaluation of Perilla Seed Oil," Food Chemistry 2000, vol. 70, pp. 13-16.

Aker Biomarine, "Superba Krill Oil—Frequently Asked Questions," http://web.archive.org/web/2009090106552/http://www.superbakrill.com: printed Sep. 3, 2013: pp. 1-3.

Hjaltason et al. "Fish Oils and Lipids from Marine Sources" In: Modifying Lipids for Use in Food. Gunstone F.D., Ed.; Woodhead Publishing: Cambridge, 2006; pp. 57-79.

Deutsch, "Evaluation of the Effect of Neptune Krill Oil on Chronic Inflammation and Arthritic Symptoms," Journal of the American College of Nutrition, vol. 26, No. 1, pp. 38-49 (2007).

Harris, "Fish Oils and Plasma Lipid and Lipoprotein Metabolism in Humans: A Critical Review," Journal of Lipid Research, vol. 30, No. 6, 1989, pp. 785-807.

Bunea et al., "Evaluation of the Effects of Neptune Krill Oil on the Clinical Course of Hypedipidemia," Alternative Medicine Review, vol. 9, No. 4, 2004, pp. 420-428.

Tou et al., "Krill for Human Consumption: Nutritional Value and Potential Health Benefits," Nutrition Reviews, vol. 65, No. 2, Feb. 2007, pp. 63-77.

Anonymous, "Krill Oil Cholesterol Study Brings Breakthrough Results," Dec. 23, 2008, Retrieved from the Internet: http://web.archive.org/web/20081223105203/http://www.krill-oil-benefits.com/krill-oil-cholesterol.php, 3 pages.

Anonymous, "Astaxanthin: The Super Antioxidant that Makes Neptune Krill Oil the Disease-Fighting, Inflammation-Fighting, PMS-Relieving, Anti-Aging Wander Supplement for Every Body," Sep. 21, 2008, Retrieved from the Internet: http://web.arhive.org/web/20080921180826/http://www.krill-oil-benefits.com/astaxanthin.php , 2 pages.

Anonymous, "Antioxidants: The "Free Radical Scavengers" Believed to Slow the Aging Clock and Protect Against Many Health Problems," Dec. 5, 2008, Retrieved from the Internet: http://web.archive.org/web/20081205014602/http://www.krill-oil-benefits,com/antioxidants.php, 2 pages.

Brigitte Gavio "Grateloupia Turuturu (Halymeniaceae, Rhodophyta) is the Correct Name of the Non-Native Species in the Atlantic Known as Grateloupia Doryphora," Eur. J. Phycol. (2002), 37: 349-359.

Kagan et al. "Acute appearance of fatty acids in human plasma-a comparative study between polar-lipid rich oil from the microalae Nannochloropsis oculats and krill oil in healthy young mails" Health and Disease 2013, 12:102 http://www.lipidworld.com/content/12/1/02; pp. 1-10.

Lee et al., "Astaxanthin Inhibits Nitric Oxide Production and Inflammatory Gene Expression by Suppressing IkB Kinase-Dependent NF-kB Activation," Molecules and Cells, Jun. 2003, vol. 16, No. 1, pp. 97-105.

(56) References Cited

OTHER PUBLICATIONS

Ohgami et al., "Effects of Astaxanthin on Lipopolysaccharide-Induced Inflammation In Vitro and In Vivo," Investigative Opthalmology & Visual Science, Jun. 2003, vol. 44, No. 6, pp. 2694-2701.
Khozin-Goloberg et al. Biosynthesis of eicosapentaenoic acid (EPA) in the freshwater eustigmatophyte monodus subterraneus (uestigmatophyceae) J.Phycol. 38, 745-756 (2002).
Harris, "Omega-3 fatty acids and cardiovascular disease: A case for omega-3 index as a new risk factor" Pharmacol. Res, vol. 55, Issue 3, Mar. 2007, pp. 217-223. Abstract Only.
Bjorndal et al., Lipids in Health Disease, 2014, 13:82. http://www.lipidworld.com/content/13/1/82.
Renstrøm B., G. Borch, O. Skulberg and S. Liaane-Jensen, "Optical Purity of (3S,3'S) Astaxanthin From Haematococcus Pluvialis," Phytochemistry, 20(11): 2561-2564, 1981. Abstract Only.
Andrewes A. and M. Starr entitled, "(3R,3'R)-Astaxanthin from the Yeast Phaffia Rhodozyma," Phytochemistry, 15:1009 1011, 1976. Abstract Only.
Turujman, S, W. Warner, R. Wei and R. Albert entitled, "Rapid Liquid Chromatographic Method to Distinguish Wild Salmon From Aquacultured Salmon Fed Synthetic Astaxanthin," J. AOAC Int., 80(3): 622-632, 1997. Abstract Only.
Schiedt, K., S. Bischof and E. Glinz entitled, "Metabolism of Carotenoids and in vivo Racemization of (3S,3'S)-Astaxanthin in the Crustacean Penaeus," Methods in Enzymology, 214:148-168, 1993. Abstract Only.
Østerlie, M., B. Bjerkeng and S. Liaan-Jensen, entitled "Plasma Appearance and Distribution of Astaxanthin E/Z and R/S Isomers in Plasma Lipoproteins of Men After Single Dose Administration of Astaxanthin," J. Nutr. Biochem, 11:482-490, 2000. Abstract Only.
Coral-Hinostroza, G., T. Ytestoyl, B. Ruyter and B. Bjerkeng entitled, "Plasma Appearance of Unesterified Astaxanthin Geometrical E/Z and Optical R/S Isomers in Men Given Single Doses of a Mixture of Optical 3 and 3'R/S Isomers of Astaxanthin Fatty Acyl Diesters," Comp. Biochem Phys. C., 139:99-110, 2004, Abstract Only.
Goldberg et al. "Biosynthesis of Eicosapentaenoic Acid (EPA) in the Fresh Water Eustigmatophyte Monodus Subterraneus (Eustigmatophyceae)," J. Phycol, 38, 745-756 (2002), same as NPL # 31 (2 copies were provided).
Mason et al., "Rofecoxib Increases Susceptibility of Human LDL and Membrane Lipids to Oxidative Damage: A Mechanism of Cardiotoxicity," Cardiovasc Pharmacol, vol. 47, Supplement 1, 2006, pp. S7-S14.
Kidd, "Astaxanthin, Cell Membrane Nutrient With Diverse Clinical Benefits and Anti-Aging Potential," Alternative Medicine Review, vol. 16, No. 4, pp. 355-364.
Nakagawa et al., "Antioxidant Effect of Astaxanthin on Phospholipid Peroxidation in Human Erythrocytes," British Journal of Nutrition (2011), Nov. 26, 2010, pp. 1-9.
Fassett et al., "Astaxanthin vs. Placebo on Arterial Stiffness, Oxidative Stress and Inflammation in Renal Transplant Patients (Xanthin): A Randomised Controlled Trial," BMC Nephrology, Dec. 18, 2008, pp. 1-8.
Maoka et al., "Stereochemical Investigation of Carotenoids in the Antarctic Krill Euphausia Superba," Bulletin of the Japanese Society of Scientific Fisheries, Mar. 14, 1985, pp. 1671-1673.
Breithaupt, "Identification and Quantification of Astaxanthin Esters in Shrimp (*Pandalus borealis*) and in a Microalga (*Haematococcus pluvialis*) by Liquid Chromatography-Mass Spectrometry Using Negative Ion Atmospheric Pressure Chemical Ionization," Institut fur Lebensmittelchemie, Universitat Hohenheim, Germany, Apr. 14, 2004, pp. 1-6.
Lourith et al., "Natural Surfactants Used in Cosmetics: Glycolipids," International Journal of Cosmetic Science, 2009, 31, pp. 255-261.

\* cited by examiner

THERAPEUTIC ASTAXANTHIN AND PHOSPHOLIPID COMPOSITION AND ASSOCIATED METHOD

RELATED APPLICATION(S)

This application is a continuation-in-part of application Ser. No. 14/219,484 filed Mar. 19, 2014, which is a continuation-in-part of application Ser. No. 13/893,572, filed May 14, 2013 (now U.S. Pat. No. 8,728,531), which is a divisional application of Ser. No. 13/093,201 filed Apr. 25, 2011 (now U.S. Pat. No. 8,663,704), which is based on provisional application Ser. No. 61/329,744, filed Apr. 30, 2010, the disclosures which are hereby incorporated by reference in their entirety.

FIELD OF THE INVENTION

This invention relates to compositions and associated methods that use astaxanthin and phospholipids to treat humans.

BACKGROUND OF THE INVENTION

The use of krill and/or marine oil are disclosed in U.S. Patent Publication Nos. 2004/0234587; 2004/0241249; and 2007/0098808, the disclosures which are hereby incorporated by reference in their entirety, and discussed in related U.S. patent application Ser. Nos. 12/840,372 and 13/079,238. The beneficial aspects of using krill and/or marine oil are shown also in a research paper published by L. Deutsch as "Evaluation of the Effect of Neptune Krill Oil on Chronic Inflammation and Arthritic Symptoms," published in the Journal of the American College of Nutrition, Volume 26, No. 1, 39-49 (2007), the disclosure which is hereby incorporated by reference in its entirety.

The published '587, '249 and '808 applications discuss the beneficial aspects of using krill oil in association with pharmaceutically acceptable carriers. As an example, this krill and/or marine oil can be obtained by the combination of detailed steps as taught in the '808 application, by placing krill and/or marine material in a ketone solvent, separating the liquid and solid contents, recovering a first lipid rich fraction from the liquid contents by evaporation, placing the solid contents and organic solvent in an organic solvent of the type as taught in the specification, separating the liquid and solid contents, recovering a second lipid rich fraction by evaporation of the solvent from the liquid contents and recovering the solid contents. The resultant krill oil extract has also been used in an attempt to decrease lipid profiles in patients with hyperlipidemia. The '808 publication gives details regarding this krill oil as derived using those general steps identified above.

SUMMARY OF THE INVENTION

Commonly assigned great-grandparent and grandparent U.S. Pat. Nos. 8,663,704 and 8,728,531, the disclosures which are hereby incorporated by reference in their entirety, are directed to the advantageous use of krill oil and astaxanthin used to treat low density lipoprotein (LDL) oxidation. Use of krill oil was a focus of the '704 and '531 patents. Further development has been accomplished with different algae species that produce EPA alone or EPA and DHA (Docosahexaenoid Acid). Further development has been accomplished using phospholipid sources and a roe extract and other surfactants.

A dietary supplement composition includes a therapeutic amount of astaxanthin and at least one of a phospholipid, glycolipid, and sphingolipid, and formulated into an oral dosage form. The astaxanthin is 0.1 to 15 percent by weight of the at least one phospholipid, glycolipid, and sphingolipid. The astaxanthin may be derived from a synthetic or natural ester or synthetic diol in an example. In another example, the dietary supplement composition is formulated to treat a cardiovascular disease, disorder or impairment in humans. In another example, it is formulated to treat a neurological disease, disorder or impairment in humans. In yet another example, it is formulated to treat a cognitive disease, disorder or impairment in humans or treat a dermatological disease, disorder or impairment in humans. It can be formulated to treat an inflammatory joint disease, disorder, or impairment or joint pain in humans.

The dietary supplement composition may include a pharmaceutical or food grade diluent. The phospholipid may include at least one of Phosphatidylcholine, Phosphatidylethanolamine, Phosphatidylserine, Phosphatidylinositol, Phosphatidic acid, Lyso-Phosphatidylcholine, Lyso-Phosphatidylethanolamine, and Lyso-Phosphatidylserine, in an example. The phospholipid may be derived from at least one of a plant, algae and animal source or synthetic derivative. The composition may include 0.5 to 12 mg of astaxanthin and 50 to 500 mg of the at least one of phospholipid, glycolipid and sphingolipid. The dietary supplement composition may be formulated into a single dosage capsule.

In another example, the dietary supplement composition includes a therapeutic amount of astaxanthin derived from a synthetic ester or diol, and at least one of a phospholipid, glycolipid, and sphingolipid, and formulated into an oral dosage form. The astaxanthin is 0.1 to 15 percent by weight of the at least one phospholipid, glycolipid, and sphingolipid. The composition is formulated to treat low density lipoprotein (LDL) oxidation in humans.

A method to treat low density lipoprotein (LDL) oxidation in humans includes administering a therapeutic amount of a dietary supplement composition comprising 0.5 to 12 mg of astaxanthin derived from a synthetic ester or diol, and at least one of a phospholipid, glycolipid, and sphingolipid, and formulated into an oral dosage form, wherein the astaxanthin is 0.1 to 15 percent by weight of the at least one phospholipid, glycolipid and sphingolipid.

DETAILED DESCRIPTION OF THE PREFERRED EMBODIMENTS

The present invention will now be described more fully hereinafter in which preferred embodiments of the invention are described. This invention may, however, be embodied in many different forms and should not be construed as limited to the embodiments set forth herein. Rather, these embodiments are provided so that this disclosure will be thorough and complete, and will fully convey the scope of the invention to those skilled in the art.

There now follows a description of the dietary supplement composition and associated method used to improve blood lipid profiles and reduce low density lipoprotein (LDL) per-oxidation in humans discussed in the respective great grandparent and grandparent '704 and '531 patents disclosed in those patents, followed by further details of a phospholipid and then a description of the algae based oil and its composition having phospholipid and glycolipid bound EPA or EPA and DHA. The description proceeds with details of the disclosure in the '704 and '531 patents regarding the use of krill oil included in the composition, and then proceed with the description and details of the phospholipid enriched delivery mechanism for astaxanthin and then algae based oil. Some of the composition components will change such as the levels of EPA and/or EPA and DHA and other components when the algae based oil is used as later shown in various tables within the following description.

The composition as related to the krill oil disclosure in the parent and grandparent '704 and '531 patents includes EPA and DHA functionalized as marine phospholipids and acyl-triglycerides derived from krill. A krill, algae, roe extract, fish oil, and phospholipid compositions, in accordance with a non-limiting example, however, may include natural or synthetic or from a synthetic diol esterified astaxanthin. It has been found that a new and potentially quite important biomarker for cardiovascular risk is related to the amount of EPA and DHA found in red blood cells divided by the total fatty acid content in red blood cells or the so called "omega-3 index." The compositions, in accordance with a non-limiting example, improve the omega-3 index in man on prolonged administration and therefore are presumed to lower cardiovascular event risks. Some of these components as related to the krill oil are explained in the following chart:

| Components | Percentage (%) |
|---|---|
| PHOSPHOLIPIDS | |
| PC, PE, PI, PS, SM, CL | >40 |
| OMEGA-3 (functionalized on PL) | >30 |
| Eicosapentaenoid Acid (EPA)* | >17 (15% in one example and 10% in another) |
| Docosahexaenoid Acid (DHA)+ | >11 (9% in one example and 5% in another) |
| ANTIOXIDANTS | (mg/100 g) |
| Astaxanthin, Vitamin A, Vitamin E | >1.25 |

*>55% of PL-EPA/Total EPA
+>55% of PL-DHA/Total DHA
These amounts can vary depending on application and persons.

The krill oil or algae based oil and other phospholipids as disclosed is supplemented with astaxanthin to improve formulated product utility. In one study, 4 mg of astaxanthin per day for two weeks resulted in a 26% reduction of LDL cholesterol oxidation. 4 mg of astaxanthin for eight weeks resulted in a 21% decrease in C-reactive protein scores. 3.6 mg of astaxanthin per day for two weeks demonstrated that astaxanthin protects LDL cholesterol against induced in vitro oxidation.

Astaxanthin is also known to reduce C-Reactive Protein (C-RP) blood levels in vivo. For example, in human subjects with high risk levels of C-RP three months of astaxanthin treatment resulted in 43% drop in the patient population's serum C-RP levels a drop which is below the unacceptable cardiovascular event risk level. Astaxanthin is so powerful that it has been shown to negate the pro-oxidant activity of Vioxx in vitro, a COX-2 inhibitor belonging to the NSAIDS drug class which is known to cause cellular membrane lipid per-oxidation leading to heart attacks and strokes. For this reason Vioxx was subsequently removed from the US market by the FDA. Astaxanthin is also absorbed in vitro by lens epithelial cells where it suppresses UVB induced lipid per-oxidative mediated cell damage at umol/L concentrations. Reduction of C-Reactive protein (CRP), reduction of LDL oxidation and an increase in the omega-3 index in vivo would presumably all be important positive contributors to cardiovascular health since each are well know biomarkers for cardiovascular health risk. These results have been shown in:

1) Lee et al., Molecules and Cells, 16(1):97-105; 2003;
2) Ohgami et al., Investigative Ophthalmology and Visual Science 44(6):2694-2701, 2003;
3) Spiller et al., J. of the Amer. College of Nutrition, 21(5): October 2002; and
4) Harris, Pharmacol. Res. 2007 March; 55(3) 217-223.

The composition includes 300-500 mg of krill oil or an algae based oil and 2 mg astaxanthin. Up to 8 mg and possibly 12 mg may be used in some examples. It may include 300-500 mg of at least one of a phospholipid, glycolipid, and sphingolipid.

Krill oil is typically produced from Antarctic krill (*euphausia superba*), which is a zooplankton (base of food chain). It is one of the most abundant marine biomass of about 500 million tons according to some estimates. Antarctic krill breeds in the pure uncontaminated deep sea waters. It is a non-exploited marine biomass and the catch per year is less than or equal to about 0.02% according to some estimates.

It is believed that Krill oil based phospholipid bound EPA and DHA uptake into cellular membranes is far more efficient than triacylglyercide bound EPA and DHA since liver conversion of triacylglycerides is itself inefficient and because phospholipid bound EPA and DHA can be transported into the blood stream via the lympathic system, thus, avoiding liver breakdown. In addition, krill oil consumption does not produce the burp-back observed with fish oil based products. Because of this burp-back feature of fish oils, it has been found that approximately 50% of all consumers who try fish oil never buy it again.

Astaxanthin has an excellent safety record. A conducted study obtained the results as follows:
Oral LD 50: 600 mg/kg (rats);
NOAEL: 465 mg/kg (rats); or
Serum Pharmacokinetics: Stewart et al. 2008
1) $T_{1/2}$: 16 hours;
2) $T_{max}$: 8 hours;
3) $C_{max}$: 65 µ/L.

At eight weeks of supplementation at 6 mg per day, there was no negative effect in healthy adults. Spiller et al. 2003.

In accordance with one non-limiting example, astaxanthin has three prime sources. 3 mg astaxanthin per 240 g serving of non-farmed raised salmon or a 1% to 12% astaxanthin oleoresin or 1.5-2.5% beadlet derived from microalgae. Literature references pertinent to the above discussion can be found in Lee et al., Molecules and Cells 16(1): 97-105, 2003; Ohgami et al., Investigative Ophthalmology and Visual Science 44(6): 2694-2701, 2003; Spiller at al., J. of the American College of Nutrition 21(5): October 2002; and Fry at al., University of Memphis, Human Performance Laboratories, 2001 and 2004, Reports 1 and 2.

Many beneficial and synergistic effects are now being reported herein have been observed when krill oil is used in combination with other active ingredients, and more specifically in one example, krill oil in combination with astaxanthin. It should be understood that different proportions of ingredients and percentages in compositions can be used depending on end use applications and other environmental and physiological factors when treating a patient condition.

The krill oil in one example is derived from *Euphasia* spp., comprising Eicosapentaenoic (EPA) and Docosahexaenoic (DHA) fatty acids in the form of triacylglycerides and phospholipids, although not less than 1% EPA and 5% DHA has been found advantageous. In another example, the krill oil includes at least 15% EPA and 9% DHA, of which not less than 45% are in the form of phospholipids, and in one example, greater than 50%. The composition can be delivered advantageously for therapeutic results with 1-4000 mg of krill oil delivered per daily dose. In another example, 0.1-50 mg astaxanthin are supplemented to the krill oil per daily dose, and in one example, 0.1-12 mg of astaxanthin.

The astaxanthin is derived from *Haematococcus pluvialis* algae, *Pfaffia*, krill, or by synthetic routes, in the known free diol, monoester or diester form, and in one example, at a daily dose of 0.5-8 mg. When this amount of astaxanthin, especially as derived from *Haematococcus pluvialis*, is applied to the range of 300-500 mg of krill oil or algae based oil, the numerical range of about 0.1 to 2.7 percent by weight of the krill oil or algae based oil is obtained.

The composition may also include an n–3 (omega-3) fatty acid rich oil derived from fish oil, algae oil, flax seed oil, or chic seed oil when the n–3 fatty acid comprises alpha-linolenic, stearidonic, eicosapentaenoic or docosapentaenoic acid. The composition may include naturally-derived and synthetic antioxidants that are added to retard degradation of fatty acids and astaxanthin.

Details of a type of CO2 extraction and processing technology (as supercritical CO2 extraction) and peroxidation blocker technology that can be used are disclosed in commonly assigned U.S. Patent Publication Nos. 2009/0181127; 2009/0181114; and 2009/0258081, the disclosures which are hereby incorporated by reference in their entirety.

As noted before, there are beneficial aspects of using krill oil or algae based oil in synergistic combination with other ingredients. It has also been determined that a fish oil derived, choline based, phospholipid bound omega-3 fatty acid mixture including phospholipid bound polyunsaturated EPA and DHA is also advantageous for improving blood lipid profiles and reducing LDL either alone or admixed with other ingredients, for example, an LDL per-oxidation blocker. One commercially available example of a mixture of fish oil derived, choline based, phospholipid bound fatty acid mixture including polyunsaturated EPA and DHA is Omega Choline 1520F as a phospholipid, omega-3 preparation, which is derived from natural fish oil and sold by Enzymotec Ltd. One example of such composition is described below:

Ingredients (g/100 g):

| | |
|---|---|
| Pure Marine Phospholipids | n.l.t. 15 |
| DHA* | n.l.t. 12 |
| EPA** | n.l.t. 7 |
| Omega-3 | n.l.t. 22 |
| Omega-6 | <3 |

*Docosahexaenoic acid
**Eicosapenteanoic acid

Analytical Data:

| | |
|---|---|
| Peroxide value (meq/Kg) | n.m.t. 5 |
| Loss on Drying (g/100 g) | n.m.t. 2 |

Physical Properties:

| | |
|---|---|
| Consistency | Viscous Liquid |

In accordance with a non-limiting example, the method improves blood lipid profiles and either alone or in combination with added astaxanthin, such as a per-oxidation blacker, and reduces LDL oxidation in a patient by administering a therapeutic amount of a composition including a mixture of fish oil derived, choline based, phospholipid bound omega-3 fatty acid mixture including phospholipid bound polyunsaturated EPA and DHA either alone or admixed with an LDL per-oxidation blocker such as astaxanthin. In one example, the composition is supplemented in combination with astaxanthin in an oral dosage form. The mixture of fish oil derived, choline based, phospholipid bound fatty acid mixture including polyunsaturated EPA and DHA in one example comprises Eicosapentaenoic (EPA) and Docosahexaenoic (DHA) fatty acids in the form of triacylglycerides and phospholipids. In another example, the omega choline includes at least 7% EPA and 12% DHA, of which not less than 15% are in the form of phospholipids. The composition can be delivered advantageously for therapeutic results with 1-4000 mg of a mixture of fish oil and fish oil derived, choline based, phospholipid bound fatty acid mixture including polyunsaturated EPA and DHA delivered per daily dose. In another example, 0.1-20 mg astaxanthin are supplemented to the Omega Choline per daily dose.

It should be understood that an instant formulation can be used for LDL reduction using only a mixture of fish oil derived, choline based, phospholipid bound fatty acid mixture including polyunsaturated EPA and DHA. It is also possible to use a mixture of fish oil derived, choline based, phospholipid bound omega-3 fatty acid mixture (including polyunsaturated EPA and DHA) mixed with astaxanthin. It should also be understood that an enriched version of a mixture of fish oil derived, choline based, phospholipid bound fatty acid mixture including polyunsaturated EPA and DHA can be used wherein the fraction of added fish oil diluents has been decreased and the proportion of fish oil derived phospholipids has been increased. This can be accomplished by using supercritical CO2 and/or solvent extractions for selective removal of triacylglycerides from phospholipids. The composition may also include a natural or synthetic cyclooxygenase-1 or -2 inhibitor comprising for example aspirin, acetaminophen, steroids, prednisone, or NSAIDs. The composition may also include a gamma-linoleic acid rich oil comprising Borage (*Borago officinalis* L.) or Safflower (*Carthamus tinctorius* L.), which delivers a metabolic precursor to $PGE_1$ synthesis.

The composition may also include an n-3 (omega-3) fatty acid rich oil derived from fish oil, algae oil, flax seed oil, chia seed oil or *perilla* seed oil wherein the n-3 fatty acid source comprises alpha-linolenic, stearidonic, eicosapentaenoic or docosapentaenoic acid. The composition may include naturally-derived and synthetic antioxidants that are added to retard degradation of fatty acids such as tocopherols, tocotrienols, carnosic acid or carnosol and/or astaxanthin.

Large dosages of astaxanthin alone have been found effective to treat osteoarthritis and joint pain. For example, one clinical trial such as described in commonly assigned U.S. Pat. No. 8,481,072, the disclosure which is hereby incorporated by reference in its entirety, uses 15 mg of astaxanthin. It has now been determined that lower dosages of astaxanthin may be used instead of these much higher dosages such as 15 mg as in some clinical trials for osteoarthritis or other uses, including cardiovascular treatment, when it is added with at least one of a phospholipid, glycolipid, and sphingolipid or other phospholipids. A pharmaceutical or food grade diluent may be added or other surfactant. Other beneficial and often synergistic results are obtained when astaxanthin is used in the presence of other components, including low molecular weight hyaluronic acid or UC-II. Phospholipids may include plant based phospholipids such as from lecithin and lysophospholipids and/or glycophospholipids, including *perilla* oil such as described in commonly assigned U.S. Pat. No. 8,784,904, the disclosure which is hereby incorporated by reference in its entirety. Astaxanthin levels could very from 0.5-2 mg and 0.5-4 mg and in one embodiment is 2-4 mg or 2-6 mg and as broad as 0.5-12 mg and 7-12 mg.

It has also been found advantageous to use herring roe extract as the source of phospholipids that may have some EPA and DHA. Synergistic results are obtained and vast improvements seen. One study indicated that phospholipids from herring roe improved phospholipid and glucose tolerance in healthy, young adults as published by Bjorndal et al., Lipids in Health Disease, 2014, 13:82. The pure roe phospholipid may be formed using extraction techniques. It is a honey-like product that is thinned or diluted with fish oil and/or *perilla* oil or other seed or plant oil, in an example.

The specification prior to dilution with fish oil and/or *perilla* oil is as follows:

| Percentage that is phospholipids | 60 |
|---|---|
| Phospholipid mg/g | 600 |
| Phosphatidyl choline portion mg/g | 520 |
| Choline equivalents | 83 |
| Total EPA mg/g (TG & PL bound) | 75 |
| Total DHA mg/g (TG & PL bound) | 195 |
| EPA mg/g bound to phospholipid | 67 |
| DHA mg/g bound to phospholipid | 175 |
| EPA + DHA mg/g bound to phospholipid | 242 |

The herring roe extract is processed in one example using extraction by ethanol. Triacylglycerides are added and ethanol stripped out to have a robust solution. Seed oil, such as the *perilla* seed oil as described in the incorporated by reference '904 patent, may be added back to the ethanol extract before stripping to thin and form a high level phospholipid blend. The roe oil extract may be mixed with fish oil and/or seed oil, such as the *perilla*, or any other marine oil. In an example, the herring egg roe extract is mixed with *perilla* seed oil of at least 1:1 and preferably as high as 6:1 ALA to LA with the concentrate as having at least 50%, and in another example 60% phospholipids, and in another example at least 30%, and in another example 40% triglycerides.

An example composition includes a combination of a roe extract from herring or a phospholipid rich roe extract with phospholipid bound EPA and DHA admixed with seed/fish oil and/or seed oil where the seed oil has a ratio of ALA to LA between 1:1 and 1:6, and including astaxanthin in one example of about 2-4 mg or 0.5 to 12 mg or other ranges as noted above. The amount of roe egg extract mixed with the seed oil such as *perilla* oil varies and is about 150 to 500 mg, or 300 to 500 mg, or up to 1,000 mg daily dose in one example and may include hyaluronic acid. Other plant based phospholipids may be used, including commercially available lecithins and an egg yolk derivative, including lysophospholipids and glycophospholipids to act as surfactants. It is possible to use sunflower-based phospholipids and natural plant-based oils and natural surfactant extracts. The astaxanthin is enhanced with fats, surfactants, or phospholipids and can be delivered more efficiently with phospholipids and sunflower based and/or the lipophilic *perilla* oil as described before.

In an example, the *perilla* oil is formed as a shelf stable, supercritical, CO2 fluid extracted seed oil derived from a cracked biomass of *perilla frutescens* from 60 to 95 percent w/w of PUFAs in a ratio of from 4:1 to 6:1 alpha-linolenic acid (ALA) to linoleic acid (LA). The *perilla frutescens* derived seed oil is made in an example by subjecting the *perilla frutescens* seed to supercritical fluid CO2 extraction to produce a seed oil extract; fractionating the resulting seed oil extract in separate pressure step-down stages for collecting light and heavy fractions of seed oil extract; and separating the heavy fraction from the light fraction to form the final seed oil from the heavy fraction.

Selected antioxidants are included in another example and the *perilla* oil includes a mixture of selected lipophilic and hydrophilic antioxidants. Lipophilic antioxidants can be used either alone or in combination with at least one of: a) phenolic antioxidants including at least one of sage, oregano, and rosemary; b) tocopherol; c) tocotrienol(s); d) carotenoids including at least one of astaxanthin, lutein, and zeaxanthin; e) ascorbylacetate; f) ascorbylpalmitate; g) Butylated hydroxytoluene (BHT); h) Docosapentaenoic Acid (BHA); or i) Tertiary Butyl hydroquinone (TBHQ). A hydrophilic antioxidant or sequesterant may include hydrophilic phenolic antioxidants including at least one of grape seed extract, tea extracts, ascorbic acid, citric acid, tartaric acid, and malic acid.

In one example, a peroxide value of this *perilla* seed oil is under 10.0 meq/Km. In another example, this *perilla* seed oil is from 85 to 95 percent w/w of PUFAs and the PUFAs are at least greater than 56 percent alpha-linolenic acid (ALA). The *perilla* seed oil is shelf stable at room temperature up to 32 months. In another example, this *perilla* seed oil is derived from a premilled or flake-rolled cracked biomass of *perilla frutescens*. The mixture of selected antioxidants may include astaxanthin, phenolic antioxidants and natural tocopherols. The *perilla* seed oil may also include at least one of dispersed nano- and micro-particles of rice or sugar cane based policosanol.

In an example, the composition is encapsulated into a single dosage capsule and referred to as a deep ocean caviar capsule. In a specific example, the encapsulated composition includes herring caviar phospholipid extract (herring roe) *perilla* (*perilla frutescens*) seed extract, olive oil, Zanthin® astaxanthin (*Haematococcus pluvialis* algae extract), gelatin, spice extract, non-GMO natural tocopherols, cholecalciferol, riboflavin, and methylcobalamin. The composition includes fish as herring roe and tilapia gelatin. It may include low molecular weight hyaluronic acid as an additive for joint care. An example is set forth in the following chart. Properties:

| Appearance | Size 00 clear capsule with dark red oily fill |
|---|---|
| Fatty Acids | |
| ALA | min. 140 mg |
| EPA | min. 18 mg |
| DHA | min. 50 mg |
| Total Omega-3 | min. 210 mg |
| Phospholipids | 195 mg |
| Astaxanthin | 500 µg |
| Vitamin $D_3$ | 1000 IU; 250% DV |
| Vitamin $B_2$ (Riboflavin) | 1.7 mg; 100% DV |
| Vitamin $B_{12}$ | 6 µg; 100% DV |
| Microbiological | USP <61>/FDA BAM |
| Total Plate Count | <1000 cfu/g |
| Yeast & Mold | <100 cfu/g |
| E. coli | Absent in 10 g |

-continued

| | |
|---|---|
| Salmonella | Absent in 10 g |
| S. aureus | Absent in 10 g |
| Storage | |
| Conditions | Tightly closed containers, 15-30° C., 30-50% RH |
| Shelf-life | 24 months minimum |
| Packaging | HDPE or PET bottle (count TED) |

All ingredients BSE-free and non-GMO

The processing components may contain a mix of marine omega-3 phospholipids derived from herring caviar and *perilla* seed oil. It may contain an O2B™ botanical peroxidation blocker, including spice extract, non-GMO tocopherols and ascorbyl palmitate. It can be packaged as a bulk product in sealed drums 45 and 190 kg net with inert headspace, complying with European and American standards for food products. It preferably stores at below room temperature. The product is protected against light and heat. If drums are opened for sampling, the headspace can be flushed with inert gas during sampling and prior to storing.

| Test | Unit | Acceptance Criterion | Method |
|---|---|---|---|
| Appearance | | Amber viscous oil | AM2020 |
| Solubility | | Oil soluble and water dispersible | AM2021 |
| | | Minimum  Maximum | |
| ALA (C18:3 n-3) | mg/g as TG[3] | 230 | AM1044 |
| EPA (C20:5 n-3) | mg/g as TG[3] | 30 | AM1001 |
| DHA (C22:6 n-3) | mg/g as TG[3] | 85 | AM1001 |
| Total omega-3[1] | mg/g as TG[3] | 370 | AM1001 |
| ALA (C18:3 n-3) | mg/g as FFA[4] | 215 | AM1044 |
| EPA (C20:5 n-3) | mg/g as FFA[4] | 28 | AM1001 |
| DHA (C22:6 n-3) | mg/g as FFA[4] | 80 | AM1001 |
| Total omega-3[1] | mg/g as FFA[4] | 335 | AM1001 |
| Total PC | mg/g | 250 | AM1002 |
| Total PL | mg/g | 300 | AM1002 |
| Total neutral lipids | mg/g | 700 | AM1003 |
| Water content by Karl Fisher | % | 3.0 | AM1004 |
| Peroxide value | meq/kg | 10.0 | AM1005 |
| Heavy metals (sum of Pb, Hg, Cd & In-organic As)[2] | mg/kg | 10 | AM1015 |

[1] Total n-3: ALA, EPA, DHA, 18:4, 20:4, 21:5, 22:5
[2] Frequency analysis
[3] All ALA, EPA, DHA or Total omega-3 expressed as triglycerides
[4] All ALA, EPA, DHA or Total omega-3 expressed as free fatty acids It has been surprisingly found that the astaxanthin may be made more bioavailable when incorporated or used with one of at least a phospholipid, glycolipid, and sphingolipid and optionally with food and/or pharmaceutical grade diluents. Lower dosages as compared to the 15 mg used in previous clinical trials for joint pain are used since the phospholipid enhances delivery. The astaxanthin is at least about 0.1 to about 15 percent by weight of the at least one phospholipid, glycolipid, and sphingolipid. The astaxanthin in an example is derived from a natural or synthetic ester or synthetic diol. A pharmaceutical or food grade diluent may be added. It can be used to treat various disorders, including cardiobascivar, neurological, cognitive, dermatological diseases, disorders or impairments, and joint pain problems. When incorporated with a microbial fermented, low molecular weight hyaluronic acid or sodium hyaluronate (hyaluronan) as described before, a dietary supplement composition is formed and can be formulated in a therapeutic amount to treat and alleviate symptoms of joint pain in a person having joint pain.

It should be understood that the triglycerides have two types of molecules as a glycerol and three fatty acids, while the phospholipids contain glycerol and fatty acids, but have one glycerol molecule and two fatty acid molecules. In place of that third fatty acid, a polar group is instead attached to the glycerol molecule so that the phospholipids are partly hydrophilic as compared to hydrophobic triglycerides. Lysophospholipids may be used as a derivative of a phospholipid in which one or both acyl derivatives have been removed by hydrolysis. Lecithin and its derivatives may be used as an emulsifier and surfactant as a wetting agent to reduce surface tension of liquids. Other phospholipids may be used. Different phospholipids include phosphatidylcholine, phosphatidylethanolamine, phosphatidylserine, phosphatidylinositol, phosphatidic acid, lyso-phosphatidylcholine, lyso-phosphatidylethanolamine, and lyso-Phosphatidylserine. Some may be derived from egg yolk and extracted chemically using hexane, ethanol, acetone, petroleum ether or benzene, and also extracted mechanically, including from different sources such as soybeans, eggs, milk, marine sources, and sunflower. When derived from soya and sunflower, phospholipids may include those products mentioned before, including phosphatidic acid. Various compositions such as lecithin may be hydrolyzed enzymatically and have a fatty acid removed by phospholipase to form the lysophospholipids that can be added to the roe extract as explained above. One phospholipase is phospholipase A2 where the fatty acid is removed at the C2 position of glycerol. Fractionation may be used.

The glycolipids are primarily derivatives of ceramides where a fatty acid is bonded or connected to the amino alcohol sphingosine. It should be understood that the phospholipid sphingomyelin is also derived from a ceramide. Glycolipids, however, contain no phosphates in comparison to the phospholipids. The fat is connected to a sugar molecule in a glycolipid and are fats bonded to sugars. Because it is built from a sphingosine, fat and sugar, some refer to it as a glycosphingolipid. A sphingolipid is a lipid that contains a backbone of sphingoid basis and set of alphatic amino alcohols that include the sphingosine. As noted before, the phospholipid and other components may be derived from at least one of a plant, algae and animal source, or a synthetic derivative thereof. The phospholipid and other components may be derived from at least one of soybean, sunflower, grapeseed, egg yolk, krill, fish body, fish roe, squid, and algae. The phospholipid and other components may be formed as compound rich mono- or di-glycerides or fatty acids where the fatty acid contains between 2 and 20 carbon atoms. During processing, the composition is formed by dispersing the astaxanthin and phospholipid and optionally a diluent under high shear conditions. The diluent may be a pharmaceutical or food grade diluent as known to those skilled in the art.

In another example, the astaxanthin is about 2 to about 10 percent by weight of the phospholipid and glycolipid and derived from a natural or synthetic ester or synthetic diol. In yet another example, 50 to 500 mg of phospholipid, glycolipid, and sphingolipid may be used. The dietary supplement composition may be formulated into a single dosage capsule.

The astaxanthin may be derived from *Haematococcus pluvialis* algae, *Pfaffia*, krill, or by synthetic routes, in the free or synthetic diol, monoester or diester form, both natural and synthetic, at a daily dose of 0.5-8 mg or 0.5-12 mg, in one example, and in another example, 1-2 mg, 2-4 mg, 1-6 mg, and other ranges, and up to 12 mg, including 7-12 mg.

The astaxanthin can vary between 2 to 4 mg or 0.5 to 12 mg and other ranges as disclosed above. It should be understood that the astaxanthin and the at least one of phospholipid, glycolipid, and sphingolipid or other components as described above may be used for many different purposes and results. It may be used to aid in treating or improving blood lipid profiles and reducing LDL per-oxidation in humans. It may be used to counter or treat depression and other neurological disorders. It may be used for respiratory illnesses and skin ailments or diseases.

The composition may also include an n-3 (omega-3) fatty acid rich oil derived from fish oil, algae oil, flax seed oil, chia seed oil, or *perilla* seed oil. In an example, the n-3 fatty acid comprises alpha-linolenic, stearidonic, eicosapentaenoic or docosapentaenoic acid. In one example composition as noted before, it has been found that an algae based oil may be used instead of krill oil. Hydrolyzed or unhydrolyzed collagen and elastin derived from eggshell membranes can also be advantageously added. The composition may also include anti-inflammatory and/or natural joint health promoting compounds comprising at least one of preparations of green lipped mussel (*Perna canaliculus*), *Boswellia serrata*, turmeric (*Curcuma longa*), stinging nettle (*Urtica dioica*), Andrographis, Cat's claw (*Uncaria tomentosa*), bromelain, methylsulfonylmethane (MSM), chondroitin sulfate, glucosamine sulfate, s-adenosyl-methionine, proanthocyanidins, procyanidins or flavonoids. The composition may include naturally-derived and synthetic antioxidants that are added to retard degradation of fatty acids and astaxanthin.

It is also possible to use a pure diol of the S, S'astaxanthin, including a synthetic diol with the surfactant and/or phospholipid. It is possible to use that pure diol in combination with the EPA rich algae based oil or other fish, roe extract, or plant based oil and/or phospholipid and/or surfactant as described above, and which is admixed with either astaxanthin derived from *Haematococcus pluvialis* or the free diol form in substantially pure S,S' enantiomer form. It is possible to add synthetically derived mixed enantiomers of the diol. The diol of the S,S'astaxanthin is possible because in cases of krill oil and algae and phospholipids and Hp derived and other types, there are principally diesters and monoesters respectively with very little diol, which is insoluble. Some research indicates that it may be many times mare bioavailable than either the monoester or diester form. It is possible to synthesize asymmetrically the S,S' pure diol. Despite the pure diol's poor solubility in some examples, there may be an active transport mechanism related to its bioavailability, or conversely, that only in the diol form is the monoester or diester forms transferred from the intestines to the blood. The phospholipid or glycolipid based product presenting EPA and/or DHA along with the added astaxanthin in its various forms and especially the S,S' enantiomeric form in principally monoester form from *Haematococcus pluvialis* or pure diol form from asymmetric synthesis could be viable. Thus, it is possible to combine it with the algae derived glycol and phospholipid based EPA rich oil.

As noted before, astaxanthin (3,3'-dihydroxy-β-β-carotene-4,4'-dione) is a xanthophyll carotenoid found in many marine species including crustaceans, salmonid fish and algae. Astaxanthin cannot be synthesized by mammals, but when consumed in the diet has shown effectiveness as an antioxidant, anti-inflammatory agent and with benefit to eye health, heart health, and the immune system.

Astaxanthin has a hydroxyl group on each β-ionone moiety, therefore it can be found in its free (diol) form as well as mono- or di-esterified. In natural products astaxanthin is commonly found as a mixture: primarily mono-esters of C12-C18 fatty acids and lesser amounts of di-ester and free diol. Synthetic astaxanthin is commonly provided in only the free diol form.

The astaxanthin molecule has two E/Z chiral centers and three optical R/S isomers. *Haematococcus pluvialis* algae produces natural astaxanthin solely in the (3S,3'S) isomer. This is explained in the article from Renstrøm B., G. Borch, O. Skulberg and S. Liaane-Jensen, "Optical Purity of (3S, 3'S) Astaxanthin From *Haematococcus Pluvialis*," Phytochemistry, 20(11): 2561-2564, 1981, the disclosure which is hereby incorporated by reference in its entirety.

Alternatively, the yeast *Phaffia rhodozyma* synthesizes only the 3R,3'R configuration. This is explained in the article from Andrewes A. and M. Starr entitled, "(3R,3'R)-Astaxanthin from the Yeast *Phaffia Rhodozyma*," Phytochemistry, 15:1009-1011, 1976, the disclosure which is hereby incorporated by reference in its entirety.

Wild salmon predominately contain the (3S,3'S) form with a (3S,3'S), (3R,3'S), and (3R,3'R) isomer ratio of 22:1:5. This is explained in the article from Turujman, S, W. Warner, R. Wei and R. Albert entitled, "Rapid Liquid Chromatographic Method to Distinguish Wild Salmon From Aquacultured Salmon Fed Synthetic Astaxanthin," J. AOAC Int., 80(3): 622-632, 1997, the disclosure which is hereby incorporated by reference in its entirety.

However, astaxanthin produced by traditional synthesis will contain a racemic mixture in a (3S,3'S), (3R,3'S; mesa), (3R,3'R) ratio of 1:2:1. This ratio is also seen in many species of shrimp, which are able to racemize (3S,3'S) to the meso form. This is explained in the article from Schiedt, K., S. Bischof and E. Glinz entitled, "Metabolism of Carotenoids and in vivo Racemization of (3S,3'S)-Astaxanthin in the Crustacean *Penaeus*," Methods in Enzymology, 214: 148-168, 1993, the disclosure which is hereby incorporated by reference in its entirety.

However, most of the astaxanthin in shrimp is within the carapace (shell) therefore limited amounts of the mesa isomer are consumed in the human diet.

Feeding studies of free diol or fatty acid esters of astaxanthin has been shown to increase the amount of astaxanthin in human plasma. This are explained in the article from Østerlie, M., B. Bjerkeng and S. Liaan-Jensen, entitled "Plasma Appearance and Distribution of Astaxanthin E/Z and R/S Isomers in Plasma Lipoproteins of Men After Single Dose Administration of Astaxanthin," J. Nutr. Biochem, 11:482-490, 2000; and the article from Coral-Hinostroza, G., T. Ytestøyl, B. Ruyter and B. Bjerkeng entitled, "Plasma Appearance of Unesterified Astaxanthin Geometrical E/Z and Optical R/S Isomers in Men Given Single Doses of a Mixture of Optical 3 and 3'R/S Isomers of Astaxanthin Fatty Acyl Diesters," Comp. Biochem Phys. C., 139:99-110, 2004, the disclosures which are hereby incorporated by reference in their entirety.

The uptake of free astaxanthin diol is about 4-5 times higher than that of esterified astaxanthin, likely due to the limitation of required enzymatic hydrolysis in the gut prior to absorption. These intestinal enzymes may also be R/S selective on astaxanthin esters. Coral-Hinostroza et al. (2004) found higher relative absorption of astaxanthin from (3R,3'R-astaxanthin dipalmitate compared to the other two isomers. However, ingestion of racemic free diol astaxanthin does not show any stereospecific selection.

Astaxanthin for use in human food supplements is currently derived from the cultivated freshwater algae *Haematococcus pluvialis*. This algae produces 3S,3'S astaxanthin ester in a fatty acid matrix which can be isolated with solvent or carbon dioxide extraction. This oily extract can be used directly in edible formulations or further processed into solid powder or beadlet preparations. Many clinical studies have been conducted with *H. pluvialis* derived astaxanthin to demonstrate beneficial health effects and safety. Food additive approvals for astaxanthin-rich algae extracts have been approved for many suppliers in the US and EU.

*Haematococcus* algae cultivation for use in dietary supplements cannot always match demand for use of astaxanthin in dietary supplements. Use of synthetic astaxanthin diol can also benefit applications which need a concentrated, standardized astaxanthin source. Conventional racemic synthetic astaxanthin sources are used as a colorant in Salmonid aquaculture as a feed ingredient. This racemic mixture may have limited use since only one-quarter of the compound is the 3S,3'S isomer commonly found in natural Salmon and has been studied in humans for efficacy and safety.

Astaxanthin may also be synthesized with in a stereospecific manner, so that the output is exclusively the generally accepted 3S,3'S isomer in a free diol form. The free diol crystals can be suspended in a vegetable oil or solid beadlet for use in edible preparations or pill, capsule, tablet form. The 3S,3'S product has the advantage of greater consistency than algal preparations and also with lower odor. Therefore algal-derived astaxanthin can be replaced with synthetic 3S,3'S astaxanthin diol in existing formulations with the same or increased effectiveness.

It has also been surprisingly found that the use of hyaluronic acid alone and/or in combination with astaxanthin is beneficial and synergistic. For example, low molecular weight hyaluronic acid in its different forms can be given to patients in an amount from 1-500 mg per day and preferably about 10-70 mg per day, and in another example, 20-60 mg, 25-50 mg, 35 mg, and 45 mg. Astaxanthin of about 2-4 mg may be added in an example, but could range from 0.5 to 4 mg a day, and 7-12 mg range in another example, or 0.5 to 12 mg. The hyaluronic acid may be given in the form of a pro-inflammatory low molecular weight sodium hyaluronate fragments that are about 0.5-300 kDa corresponding to the pro-inflammatory low molecular weight fragments. Although the use of astaxanthin and phospholipids such as from krill oil, algae oil, roe, fish oil product, or plant based oils helps in delivering the hyaluronic acid, still the low molecular weight hyaluronic acid and in the form of the fragments preferably is still small enough to enter through the gut and be used in an oral administration.

It is also advantageous to use astaxanthin with the low molecular weight hyaluronic acid. Different amounts can be used, and in one example, 2-4 mg per day, and in another example, 0.5-12 mg per day can be used with low molecular weight hyaluronic acid such as the amount of 1-500 mg and preferably about 10-70 mg and with 0.5-12 mg or 4-12 mg of astaxanthin. About 40-120 mg of low molecular weight hyaluronic acid may be used in an example. A dosage of astaxanthin may be about 6-8 mg and the low molecular weight hyaluronic acid could be in the range of about 60-80 mg. Although the greater amounts of astaxanthin may be used with low molecular weight hyaluronic acid alone, it is possible to use 2 mg of astaxanthin and lower amounts of low molecular weight hyaluronic acid such as 20 mg and up to 40 mg as non-limiting examples. It should be understood that hyaluronic acid fragments such as the pro-inflammatory low molecular weight sodium hyaluronate fragments are potent as innate immune system cell receptors signaling molecules associated with the inflammatory cascade and the oral hyaluronic acid in the form of low molecular weight fragments can reach joints as compared to the higher molecular weight hyaluronic acid that is injected since it is not orally administered.

As noted before, the composition may include with the astaxanthin and phospholipid a pro-inflammatory microbial fermented sodium hyaluronate fragments having a molecular weight of 0.3 to 300 kilodaltons (kDa), and in an example, from 0.5 to 230 kDa, and from 0.5 to 100 kDa, all in an oral dosage form for alleviating symptoms of non-disease state joint pain, but may also be used to treat and alleviate symptoms of osteoarthritis and/or rheumatoid arthritis when combined with the astaxanthin and phospholipid as described above. These polymers of hyaluronic acid or sodium hyaluronate (hyaluronan) can be derived from microbial fermentation or animal tissue. Daily dosages can vary, but can be about 1-500 mg of hyaluronan, and in an example, between 10 and 70 mg/dose and at 20 to 60, 25 to 50, and 35 and 45 mg per dose. This hyaluronan or hyaluronic acid and its fragments are micro- or nano-dispersed within the composition. In an example, the hyaluronic acid is derived from a biofermentation process or also from microbial fermentation or animal tissue.

In an example, the pure low molecular weight hyaluronic acid oligomers are fragments and derived principally and practically from microbial fermentation, but can also be derived from hydrolyzed animal tissue. This microbial fermentation process is known to produce extraordinarily pure low molecular sodium hyaluronate free from amino acid conjugation. In an example, the resulting low molecular weight hyaluronic acid is obtained from a mutant strain of *streptococcus* bacteria with the fermentation process, followed by isolation and denaturation of the organism and its proteins with ethanol and heat, followed by filtration and chemical modification of its molecular weight with acid aqueous chemical hydrolysis as a chemical reaction. The final product is isolated by ethanol precipitation of the sodium salt and drying to produce pro-inflammatory low molecular weight microbial fermented sodium hyaluronate fragments. It is a chemical reaction degradation product of a mutant strain *streptococcus* bacterial fermentation using in one example the bacterial strain *streptococcus zooepidemicus* and the production strain is a non-hemolytic mutant of a parent strain, NCTC7023. The production strain is produced by nitroso-guanidine mutagenesis with a unique ribosomal genome sequence, not naturally found in nature. The major manufacturing steps have three stages of: 1) fermentation; 2) purification; and 3) refining.

Other sources of the low molecular weight hyaluronic acid may include chicken sternal cartilage extract and may include elastin, elastin precursors, and collagen. It may be contained in a matrix form with chondroitin sulfate and naturally occurring hydrolyzed collagen Type-II nutraceutical ingredients. It may include the Type-I collagen derived from bovine collagen or chicken sternal cartilage collagen Type-II or natural eggshell membrane that includes hyaluronic acid that is processed to form low molecular weight hyaluronic acid. It may be derived from rooster combs.

It has been found surprisingly effective to use the astaxanthin and phospholipid. Synergistic effects have also been found when combined with about 50 mg of an active ingredient that includes cartilage such as Type-II collagen and hyaluronic acid and the added astaxanthin. Boron may be used. The composition may include collagen, boron, and hyaluronic acid. Astaxanthin may be used alone such as 0.5 to 4 mg, or 0.5 to 12 mg of astaxanthin plus 30-45 mg of low molecular weight hyaluronic acid, but smaller amounts can be used. A cartilage blend as a mixture of cartilage and salt may be used. The cartilage blend includes cartilage and potassium chloride to provide undenatured Type-II collagen. It may also include glucosamine hydrochloride and methylsulfonymethane (MSM). Chondroitin sulfate may be added.

It is known that algae can be an important source for omega-3 fatty acids such as EPA and DHA. It is known that fish and krill do not produce omega-3 fatty acids but accumulate those fatty acids from the algae they consume. Omega-3 bioavailability varies and is made available at the site of physiological activity depending on what form it is contained. For example, fish oil contains omega-3 fatty acids in a triglyceride form that are insoluble in water and require emulsification by bile salts via the formation of micelles and subsequent digestion by enzymes and subsequent absorption. Those omega-3 fatty acids that are bound to polar lipids, such as phospholipids and glycolipids, however, are not dependent on bile for digestion and go through a simpler digestion process before absorption. Thus, these omega-3 fatty acids, such as from an algae based oil, have greater bioavailability for cell growth and functioning as compared to the omega-3 triglycerides of fish oil. There are many varieties of algae that contain EPA conjugated with phospholipid and glycolipid polar lipids or contain EPA and DHA conjugated with phospholipids and glycolipids.

Throughout this description, the term "algae" or "microalgae" may be used interchangeably to each other with microalgae referring to photosynthetic organisms that are native to aquatic or marine habitats and are too small to be seen easily as individual organisms with the naked eye. When the term "photoautotropic" is used, it refers to growth with light as the primary source of energy and carbon dioxide as the primary source of carbon. Other forms of biomass that may encompass algae or microalgae may be used and the term "biomass" may refer to a living or recently dead biological cellular material derived from plants or animals. The term "polar" may refer to the compound that has portions of negative and/or positive charges forming negative and/or positive poles. The term "oil" may refer to a combination of fractionable lipid fractions of a biomass. As known to those skilled in the art, this may include the entire range of various hydrocarbon soluble in non-polar solvents and insoluble, or relatively insoluble in water as known to those skilled in the art. The microalgae may also include any naturally occurring species or any genetically engineered microalgae to have improved lipid production.

This algae based oil provides an algae sourced EPA or an EPA/DHA based oil in which oils are present in phospholipid and glycerolipid forms, as glycolipids. Different algae based oils derived from different microalgae may be used. One preferred example algae based oil has the EPA titre higher than the DHA as compared to a class of omega-3's from fish oils that are triacylglycerides. These algae based oils are rich in EPA and in the phospholipid and glycolipid forms. An example marine based algae oil is produced by Parry Nutraceuticals as a division of ETD Parry (India) Ltd. as an omega-3 (EPA) oil.

The following first table shows the specification of an algae based oil as manufactured by Parry Nutraceuticals identified above, followed by a second table for a fatty acid profile chart of that algae based oil. A third table is a comparative chart of the fatty acid profiles for non-algae based oils. These charts show that the algae based oil has a high EPA content of phospholipids and glycolipids. The algae based oils may be processed to enrich selected constituents using supercritical CO2 and/or solvent extractions as noted above and other techniques.

| SPECIFICATION: ALGAE BASED OIL | | | |
|---|---|---|---|
| PARAMETERS | SPECIFICATION | SOP. NO | TEST METHOD/ REFERENCE |
| Physical Properties | | | |
| Appearance | Viscous oil | QA - 88 | In house |
| Color | Brownish black | QA - 88 | In house |
| Odor | Characteristic | QA - 88 | In house |
| Taste | Characteristic | QA - 88 | In house |
| General Composition | | | |
| Loss on drying (%) | 2.0-3.0 | QA - 038 | USP <731> Loss on drying |
| Ash (%) | 0.5-1.0 | QA - 080 | AOAC Official Method 942.05, 16th Edition |
| Protein (%) | 1.0-2.0 | QA - 021 | AOAC Official method 978.04, 16th Edn. |
| Carbohydrate (%) | 1.0-2.0 | | AOAC 18th Edn 2006/By Difference |
| Residual Solvent (ppm) (as Ethyl Acetate) (as Acetone) | NMT 100 NMT 30 | QA - 074 | GC - Head Space, USP <467) |
| Lipid Composition | | | |
| Total Lipid (%) | 92.0-95.0 | QA - 86 | AOAC official method 933.08 |
| Chlorophyll (%) | NMT 1.50 | QA - 078 | Jeffrey & Humphrey (1975) - |

| SPECIFICATION: ALGAE BASED OIL | | | |
|---|---|---|---|
| PARAMETERS | SPECIFICATION | SOP. NO | TEST METHOD/ REFERENCE |
| Total carotenoids (%) | NMT 1.50 | QA - 85 | Photosynthetic pigments of Algae (1989) By JHA method-1986 |
| Total Unsaponifiables (%) | NMT 12.0 | QA - 086 | AOAC official method 933.08 |
| Omega 3 [EPA + DHA] - % w/w | NLT 15.00 | QA - 087 | In House method |
| Total Omega 3 (% w/w) | NLT 17.00 | | |
| Total Omega 6 (% w/w) | NMT 5.00 | | |
| Total EFA (% w/w) | NLT 20. | | |
| Lipid percentage | | | |
| Triglycerides | 15-20% | | |
| Phospholipids | 5-10% | | |
| Glycolipids | 35-40% | | |
| Free fatty acids | 15-20% | | |
| Microbial parameters | | QA - 039 | AOAC, 1995, Chapter 17 |
| Standard Plate Count (cfu/1 g) | NMT 1,000 | | |
| Yeast & Mold (cfu/1 g) | NMT 100 | | |
| Coli forms (/10 g) | Negative | | |
| *E. Coli* (/10 g) | Negative | | |
| *Staphylococcus* (/10 g) | Negative | | |
| *Salmonella* (/10 g) | Negative | | |
| Fatty acid profile (Area %) | | | |
| Myristic acid [14:0] | NLT 4.0 | QA - 086 & 087 | In House GC method |
| Palmiltic acid [16:0] | NLT 16.0 | | |
| Palmito oleic acid [16:1, n-9] | NLT 12.0 | | |
| Hexadecadienoic acid [16:2, n-4] | NLT 4.0 | | |
| Hexadecatrienoic acid [16:3, n-4] | NLT 12.0 | | |
| Stearic acid [18:0] | NLT 0.10 | | |
| Oleic acid [18:1] | NLT 1.0 | | |
| Linoleic acid [18:2, n-6] - LA | NLT 1.0 | | |
| AlphaLinolenic acid [18:3, n-3] - ALA | NLT 0.50 | | |
| Stearidonic acid [18:4, n-3] - SA | NLT 0.10 | | |
| Arachidonic Acid [20:4, n-6] - AA | NLT 0.25 | | |
| Eicosapentaenoic acid [20:5, n-3] | NLT 15.0 | | |
| Decosahexaenoic acid [20:6, n-3] | NLT 1.5 | | |
| Heavy Metals | | | |
| Lead (ppm) | NMT 1.0 | External lab reports | AOAC 18th Edn: 2006 By ICPMS |
| Arsenic (ppm) | NMT 0.5 | | |
| Cadmium (ppm) | NMT 0.05 | | |
| Mercury (ppm) | NMT 0.05 | | |

Safety: Safe for the intended use
Shelf life: 24 months from the date of manufacture
Stability: Stable in unopen conditions
Storage: Store in a cool, dry place away from sunlight, flush container with Nitrogen after use
Documentation: Every Batch of shipment carries COA
Packing: 1 kg, 5 kg, and 20 kg food grade containers

FATTY ACID PROFILE CHART ALGAE BASED OIL

| FATTY ACID | ALGAE BASED OMEGA-3 (EPA) OIL |
|---|---|
| Total fatty acid, gm/100 gm of oil | 75 gm |
| Fatty acid [% of total fatty acid] | |
| Myristic acid [14:0] | 6.87 |
| Pentadecanoic acid [15:0] | NA |
| Palmitic acid [16:0] | 20.12 |
| Palmito oleic acid [16:1, ω-9] | 18.75 |
| Hexadeca dienoic acid [16:2, ω-4] | 6.84 |
| Hexadeca trienoic acid [16:4, ω-4] | 12.54 |
| Heptadecanoic acid [17:0] | NA |
| Stearic acid [18:0] | 0.68 |
| Oleic acid [18:1, ω-9] | 3.56 |
| Linoleic acid [18:2, ω-6] | 2.68 |
| Alpha linolenic acid [18:3, ω-3] | 3.73 |
| Gamma linolenic acid [18:3, ω-6] | NA |
| Stearidoni acid [18:4, ω-3] | 0.33 |
| Arachidonic acid [20:4, ω-6] | 0.97 |
| Eicosapentaenoic acid [20:5, ω-3] EPA | 23.00 |
| Docosapentaenoic acid [22:5, ω-3] DHA | NA |
| Docosahexaenoic acid [22:6, ω-3] DHA | 3.26 |
| others | 3.54 |
| EPA/DHA [gm/100 gm oil] | 15.75 |
| Total ω-3 fatty acids [gm/100 gm oil] | 18.20 |
| LIPD CLASS DETAILS [gm/100 gm oil] | |
| Unsaponifiables [carotenoids, chlorophyll, sterol, fatty alcohol etc.,] | 12 |
| Free fatty acids | 20 |
| Triglydcerides | 20 |
| Phospholipids | 10 |
| Glycolipids | 38 |
| Total | 100 |
| STABILITY [months] | 24 |

FATTY ACID PROFILE - COMPARATIVE CHART NON-ALGAE BASED OILS

| FATTY ACID | FISH OIL MAXEPA | KRILL OIL | MARTEK OIL |
|---|---|---|---|
| Total fatty acid, gm/100 gm of oil | 95 gm | 70-80 gm | 95 gm |
| Fatty acid [% of total fatty acid] | | | |
| Myristic acid [14:0] | 8.68 | 11.09 | 11.47 |
| Pentadecanoic acid [15:0] | NA | NA | NA |
| Palmitic acid [16:0] | 20.35 | 22.95 | 26.36 |
| Palmito oleic acid [16:1, ω-9] | 11.25 | 6.63 | NA |
| Hexadeca dienoic acid [16:2, ω-4] | NA | NA | NA |
| Hexadeca trienoic acid [16:4, ω-4] | NA | NA | NA |
| Heptadecanoic acid [17:0] | NA | NA | NA |
| Stearic acid [18:0] | 4.67 | 1.02 | 0.50 |
| Oleic acid [18:1, ω-9] | 13.07 | 17.93 | 1.50 |
| Linoleic acid [18:2, ω-6] | 1.28 | 0.14 | 0.61 |
| Alpha linolenic acid [18:3, ω-3] | 0.33 | 2.11 | 0.40 |
| Gamma linolenic acid [18:3, ω-6] | NA | NA | NA |
| Stearidoni acid [18:4, ω-3] | 1.69 | 7.01 | 0.33 |
| Arachidonic acid [20:4, ω-6] | 0.50 | NA | NA |
| Eicosa pentaenoic acid [20:5, ω-3] EPA | 20.31 | 19.04 | 1.0 |
| Docosa pentaenoic acid [22:5, ω-3] DHA | NA | NA | 15.21 |
| Docosa hexaenoic acid [22:6, ω-3] DHA | 13.34 | 11.94 | 42.65 |
| others | 4.53 | 0.14 | NA |
| EPA/DHA [gm/100 gm oil] | 31.96 | 21.68 | 41.46 |
| Total ω-3 fatty acids [gm/100 gm oil] | 33.85 | 28.00 | 41.60 |
| LIPD CLASS DETAILS [gm/100 gm oil] | | | |
| Unsaponifiables [carotenoids, chlorophyll, sterol, fatty alcohol etc.,] | 5 | 5 | 5 |
| Free fatty acids | 0.5 | 30 | 0.5 |
| Triglydcerides | 94.5 | 25 | 94.5 |
| Phospholipids | Nil | 40 | Nil |
| Glycolipids | Nil | Nil | Nil |
| Total | 100 | 100 | 100 |
| STABILITY [months] | 12 | 24 | 6 |

Different types of marine based algae oils may be used, including *nannochloropsis oculata* as a source of EPA. Another algae that may be used is *thalassiosira weissflogii* such as described in U.S. Pat. No. 8,030,037 assigned to the above-mentioned Parry Nutraceuticals, a Division of ETD Parry (India) Ltd., the disclosure which is hereby incorporated by reference in its entirety. Other types of algae as disclosed include *chaetoceros* sp. or *prymnesiophyta* or green algae such as *chlorophyta* and other microalgae that are *diamons tiatoms*. The *chlorophyta* could be *tetraselmis* sp. and include *prymnesiophyta* such as the class *prymnesiophyceae* and such as the order *isochrysales* and more specifically, *isochrysis* sp. or *pavlova* sp.

There are many other algae species that can be used to produce EPA and DHA as an algae based oil whether marine based or not to be used in accordance with a non-limiting example. In some cases, the isolation of the phospholipid and glycolipid bound EPA and DHA based oils may require manipulation of the algae species growth cycle.

Other algae/fungi phospholipid/glycolipid sources include: *grateloupia turuturu; porphyridium cruentum; monodus subterraneus; phaeodactylum tricornutum; isochrysis galbana; navicula* sp.; *pythium irregule; nannochloropsis* sp.; and *nitzschia* sp.

Details regarding *grateloupia turuturu* are disclosed in the article entitled, "*Grateloupia Turuturu* (Halymeniaceae, Rhodophyta) is the Correct Name of the Non-Native Species in the Atlantic Known as *Grateloupia Doryphora*," Eur. J. Phycol. (2002), 37: 349-359, as authored by Brigitte Gavio and Suzanne Fredericq, the disclosure which is incorporated by reference in its entirety.

*Porphyridium cruentum* is a red algae in the family porphyridiophyceae and also termed rhodophyta and is used as a source for fatty acids, lipids, cell-wall polysaccharides and pigments. The polysaccharides of this species are sulphated. Some *porphyridium cruentum* biomass contains carbohydrates of up to 57%.

*Monodus subterraneus* is described in an article entitled, "Biosynthesis of Eicosapentaenoic Acid (EPA) in the Fresh Water Eustigmatophyte *Monodus Subterraneus* (Eustigmatophyceae)," J. Phycol, 38, 745-756 (2002), authored by Goldberg, Shayakhmetova, and Cohen, the disclosure which is incorporated by reference in its entirety. The biosynthesis of PUFAs from algae is complicated and the biosynthesis from this algae is described in that article.

*Phaeodactylum tricornutum* is a diatom and unlike most diatoms, it can grow in the absence of silicon and the biogenesis of silicified frustules is facultative.

*Isochrysis galbana* is a microalgae and used in the bivalve aquaculture industry.

*Navicula* sp. is a boat-shaped algae and is a diatom. *Pythium irregule* is a soilborne pathogen found on plant hosts.

*Nannochloropsis* sp. occurs in a marine environment, but also occurs in fresh and brackish water. The species are small, nonmotile spheres that do not express any distinct morphological feature. These algae have chlorophyll A and lack chlorophyll B and C. They can build high concentrations of pigment such as astaxanthin, zeaxanthin and canthaxinthin. They are about 2-3 micrometers in diameter. They may accumulate high levels of polyunsaturated fatty acids.

*Nitzschia* sp. is a pinnate marine diatom and usually found in colder waters and associated with both Arctic and Antarctic polar sea ice where it is a dominant diatom. It produces a neurotoxin known as domoic acid which is responsible for amnesic shell fish poisoning. It may grow exponentially at temperatures between −4 and −6 degrees C. It may be processed to form and extrapolate the fatty acids.

As a source of polyunsaturated fatty acids, microalgae competes with other micro-organisms such as fungi and bacteria. There may be some bacterial strains that could be an EPA source, but microalgae has been found to be a more adequate and readily available source. Microalgae is a good source of oil and EPA when derived from *phaeodactylum*, *isochrysis* and *monodus*. The microalgae *phaeodactylum tricornutum* produces a high proportion of EPA. Other different strains and species of microalgae, fungi and possibly bacteria that can be used to source EPA include the following:

I. Diatoms
  *Asterionella japonica*
  *Bidulphia sinensis*
  *Chaetoceros septentrionale*
  *Lauderia borealis*
  *Navicula biskanteri*
  *Navicula laevis (heterotrof.)*
  *Navicula laevis*
  *Navicula incerta*
  *Stauroneis amphioxys*
  *Navicula pellicuolsa*
  *Bidulphia aurtia*
  *Nitzschia alba*
  *Nitzschia chosterium*
  *Phaeodactylum tricornutum*
  *Phaeodactylum tricornutum*
  *Skeletonema costatum*
II. Chrysophyceae
  *Pseudopedinella* sp.
  *Cricosphaera elongate*
III. Eustigmatophyceae
  *Monodus subterraneus*
  *Nannochloropsis*
IV. Prymnesiophyceae
  *Rodela violacea* 115.79
  *Porphyry. Cruentum* 1380. Id
V. Prasinophyceae
  *Pavlova salina*
VI. Dinophyceae
  *Cochlodinium heteroloblatum*
  *Cryptecodinium cohnii*
  *Gonyaulax catenella*
  *Gyrodinium cohnii*
  *Prorocentrum minimum*
VII. Other Microalgae
  *Chlorella minutissima*
  *Isochrysis galbana* ALII4
  *Phaeodactylum tricornutum* WT
  *Porphyridium cruentum*
  *Monodus subterraneus*
VIII. Fungi
  *Mortierella alpine*
  *Mortierella alpine* IS-4
  *Pythium irregulare*
IX. Bacteria
  SCRC-2738

Different microalgae may be used to form the algae based oil comprising glycolipids and phospholipids and at least EPA and/or EPA/DHA. Examples include: Chlorophyta, Cyanophyta (Cyanobacteria), and Heterokontophyta. The microalgae may be from one of the following classes: Bacillariophyceae, Eustigmatophyceae, and Chrysophyceae. The microalgae may be from one of the following genera: *Nannochloropsis, Chlorella, Dunaliella, Scenedesmus, Selenastrum, Oscillatoria, Phormidium, Spirulina, Amphora,* and *Ochromonas*.

Other non-limiting examples of microalgae species that may be used include: *Achnanthes orientalis, Agmenellum* spp., *Amphiprora hyaline, Amphora coffeiformis, Amphora coffeiformis* var. *linea, Amphora coffeiformis* var. *punctata, Amphora coffeiformis* var. *taylori, Amphora coffeiformis* var. *tenuis, Amphora delicatissima, Amphora delicatissima* var. *capitata, Amphora* sp., *Anabaena, Ankistrodesmus, Ankistrodesmus falcatus, Boekelovia hooglandii, Borodinella* sp., *Botryococcus braunii, Botryococcus sudeticus, Bracteococcus minor, Bracteococcus medionucleatus, Carteria, Chaetoceros gracilis, Chaetoceros muelleri, Chaetoceros muelleri* var. *subsalsum, Chaetoceros* sp., *Chlamydomas perigranulata, Chlorella anitrata, Chlorella antarctica, Chlorella aureoviridis, Chlorella candida, Chlorella capsulate, Chlorella desiccate, Chlorella ellipsoidea, Chlorella emersonii, Chlorella fusca, Chlorella fusca* var. *vacuolata, Chlorella glucotropha, Chlorella infusionum, Chlorella infusionum* var. *actophila, Chlorella infusionum* var. *auxenophila, Chlorella kessleri, Chlorella lobophora, Chlorella luteoviridis, Chlorella luteoviridis* var. *aureoviridis, Chlorella luteoviridis* var. *lutescens, Chlorella miniata, Chlorella minutissima, Chlorella mutabilis, Chlorella nocturna, Chlorella ovalis, Chlorella parva, Chlorella photophila, Chlorella pringsheimii, Chlorella protothecoides, Chlorella protothecoides* var. *acidicola, Chlorella regularis, Chlorella regularis* var. *minima, Chlorella regularis* var. *umbricata, Chlorella reisiglii, Chlorella saccharophila, Chlorella saccharophila* var. *ellipsoidea, Chlorella salina, Chlorella simplex, Chlorella sorokiniana, Chlorella* sp., *Chlorella sphaerica, Chlorella stigmatophora, Chlorella vanniellii, Chlorella vulgaris, Chlorella vulgaris* fo. *tertia, Chlorella vulgaris* var. *autotrophica, Chlorella vulgaris* var. *viridis, Chlorella vulgaris* var. *vulgaris, Chlorella vulgaris* var. *vulgaris* fo. *tertia, Chlorella vulgaris* var. *vulgaris* fo. *viridis, Chlorella xanthella, Chlorella zofingiensis, Chlorella trebouxioides, Chlorella vulgaris, Chlorococcum infusionum, Chlorococcum* sp., *Chlorogonium, Chroomonas* sp., *Chrysosphaera* sp., *Cricosphaera* sp., *Crypthecodinium cohnii, Cryptomonas* sp., *Cyclotella cryptica, Cyclotella meneghiniana, Cyclotella* sp., *Dunaliella* sp., *Dunaliella bardawil, Dunaliella bioculata, Dunaliella granulate, Dunaliella maritime, Dunaliella minuta, Dunaliella parva, Dunaliella peircei, Dunaliella primolecta, Dunaliella* salina, *Dunaliella terricola*, *Dunaliella tertiolecta*, *Dunaliella viridis*, *Dunaliella tertiolecta*, *Eremosphaera viridis*, *Eremosphaera* sp., *Effipsoidon* sp., *Euglena* spp., *Franceia* sp., *Fragilaria crotonensis*, *Fragilaria* sp., *Gleocapsa* sp., *Gloeothamnion* sp., *Haematococcus pluvialis*, *Hymenomonas* sp., *Isochrysis* aff. *galbana*, *Isochrysis galbana*, *Lepocinclis*, *Micractinium*, *Micractinium*, *Monoraphidium minutum*, *Monoraphidium* sp., *Nannochloris* sp., *Nannochloropsis salina*, *Nannochloropsis* sp., *Navicula acceptata*, *Navicula biskanterae*, *Navicula pseudotenelloides*, *Navicula pelliculosa*, *Navicula saprophila*, *Navicula* sp., *Nephrochloris* sp., *Nephroselmis* sp., *Nitschia communis*, *Nitzschia alexandrina*, *Nitzschia closterium*, *Nitzschia communis*, *Nitzschia dissipate*, *Nitzschia frustulum*, *Nitzschia hantzschiana*, *Nitzschia inconspicua*, *Nitzschia intermedia*, *Nitzschia microcephala*, *Nitzschia pusilla*, *Nitzschia pusilla elliptica*, *Nitzschia pusilla monoensis*, *Nitzschia quadrangular*, *Nitzschia* sp., *Ochromonas* sp., *Oocystis parva*, *Oocystis pusilla*, *Oocystis* sp., *Oscillatoria limnetica*, *Oscillatoria* sp., *Oscillatoria subbrevis*, *Parachlorella kessleri*, *Pascheria acidophila*, *Pavlova* sp., *Phaeodactylum tricornutum*, *Phagus*, *Phormidium*, *Platymonas* sp., *Pleurochrysis carterae*, *Pleurochrysis dentate*, *Pleurochrysis* sp., *Prototheca wickerhamii*, *Prototheca stagnora*, *Prototheca portoricensis*, *Prototheca moriformis*, *Prototheca zopfii*, *Pseudochlorella aquatica*, *Pyramimonas* sp., *Pyrobotrys*, *Rhodococcus opacus*, *Sarcinoid chrysophyte*, *Scenedesmus armatus*, *Schizochytrium*, *Spirogyra*, *Spirulina platensis*, *Stichococcus* sp., *Synechoccus* sp., *Synechocystisf*, *Tagetes erecta*, *Tagetes patula*, *Tetraedron*, *Tetraselmis* sp., *Tetraselmis suecica*, *Thalassiosira weissflogii*, and *Viridiella fridericiana*. Preferably, the microalgae are autotrophic.

It is also possible to form the oil comprising glycolipids and phospholipids and at least EPA from genetically modified yeast. Non-limiting examples of yeast that can be used include: *Cryptococcus curvatus*, *Cryptococcus terricolus*, *Lipomyces starkeyi*, *Lipomyces lipofer*, *Endomycopsis vernalis*, *Rhodotorula glutinis*, *Rhodotorula gracilis*, *Candida 107*, *Saccharomyces paradoxus*, *Saccharomyces mikatae*, *Saccharomyces bayanus*, *Saccharomyces cerevisiae*, any *Cryptococcus*, *C. neoformans*, *C. bogoriensis*, *Yarrowia lipolytica*, *Apiotrichum curvatum*, *T. bombicola*, *T. apicola*, *T. petrophilum*, *C. tropicalis*, *C. lipolytica*, and *Candida albicans*. It is even possible to use a biomass as a wild type or genetically modified fungus. Non-limiting examples of fungi that may be used include *Mortierella*, *Mortierrla vinacea*, *Mortierella alpine*, *Pythium debaryanum*, *Mucor circinelloides*, *Aspergillus ochraceus*, *Aspergillus terreus*, *Pennicillium iilacinum*, *Hensenulo*, *Chaetomium*, *Cladosporium*, *Malbranchea*, *Rhizopus*, and *Pythium*, It is also possible that bacteria may be used that includes lipids, proteins, and carbohydrates, whether naturally occurring or by genetic engineering. Non-limiting examples of bacteria include: *Escherichia coli*, *Acinetobacter* sp. any actinomycete, *Mycobacterium tuberculosis*, any streptomycete, *Acinetobacter calcoaceticus*, *P. aeruginosa*, *Pseudomonas* sp., *R. erythropolis*, *N. erthopolis*, *Mycobacterium* sp., *B.*, *U. zeae*, *U. maydis*, *B. lichenformis*, *S. marcescens*, *P. fluorescens*, *B. subtilis*, *B. brevis*, *B. polmyma*, *C. lepus*, *N. erthropolis*, *T. thiooxidans*, *D. polymorphis*, *P. aeruginosa* and *Rhodococcus opacus*.

Possible algae sourced, EPA/DHA based oils that are derived from an algae and contain glycol and phospholipid bound EPA and/or EPA/DHA and may include a significant amount of free fatty acids, triglycerides and phospholipids and glycolipids in the range of 35-40% or more of total lipids are disclosed in the treatise "Chemicals from Microalgae" as edited by Zvi Cohen, CRC Press, 1999. Reference is also made to a study in men that have been given a single dose of oil from a polar-lipid rich oil from the algae *nannochloropis oculata* as a source of EPA and described in the article entitled, "Acute Appearance of Fatty Acids in Human Plasma—A Comparative Study Between Polar-Lipid Rich Oil from the Microalgae *Nannochloropis Oculata* in Krill Oil in Healthy Young Males," as published in Lipids in Health and Disease, 2013, 12:102 by Kagan et al. The EPA in that algae oil was higher than that of krill oil by about 25.06 to 13.63 for fatty acid composition as the percent of oil. The algae oil was provided at 1.5 grams of EPA and no DHA as compared to krill oil that was provided at 1.02 grams EPA and 0.54 grams DHA. The participants consumed both oils in random order and separated by seven days and the blood samples were collected before breakfast and at several time points up to 10 hours after taking the oils.

The researchers determined that the algae based oil had a greater concentration of EPA and plasma than krill oil with the EPA concentration higher with the algae based oil at 5, 6, 8 and 10 hours ($P<0.05$) intended to be higher at 4 hours ($P=0.094$). The maximum concentration (CMAX) of EPA was higher with algae oil than with krill oil ($P=0.010$). The maximum change in concentration of EPA from its fasting concentration was higher than with krill oil ($P=0.006$). The area under the concentration curve (AUC) and the incremental AUC (IAUC) was greater ($P=0.020$ and $P=0.006$). This difference may relate to the different chemical composition and possibly the presence of the glycolipids where the presence of DHA in krill oil limits the incorporation of EPA into plasma lipids. Also, the n-3 polyunsaturated fatty acids within glycolipids as found in the algae oil, but not in a krill oil, may be an effective system for delivering EPA to humans.

The incorporated by reference '037 patent describes the benefit of using an algae based oil, and more particularly, a marine based algae oil and discloses different manufacturing and production techniques. Microalgae can be cultured photoautotrophically outdoors to prepare concentrated microalgae products containing Eicosapentaenoic acid (EPA) and Docosahexaenoic acid (DHA), which are the long-chain polyunsaturated fatty acids (PUPAs) found in fish oil. Both are very important for human and animal health. The concentrated microalgae products as disclosed in the '037 patent may contain EPA and DHA and lipid products containing EPA and DHA purified from microalgae. The concentrated microalgae composition may be prepared by cultivating microalgae photoautotrophically outdoors in open ponds under filtered sunlight in a continuous or batch mode and at a dilution rate of less than 35% per day. The microalgae may be harvested in the exponential phase when the cell number is increasing at a rate of at least 20% of maximal rate. In one example, the microalgae is concentrated. In another example, at least 40% by weight of lipids in the microalgae are in the form of glycodiacylglycerides, phosphodiacylglycerides, or a combination thereof and at least 5% by weight of the fatty acids are DHA, EPA, or a combination thereof.

In one example, the microalgae are *Tetraselmis* sp. cultivated at above 20° C. or in another example at above 30° C. The EPA yield in the microalgae has been found to be at least 10 mg/liter culture. The microalgae can be *Isochrvsis* sp. or *Pavlova* sp. in another example, or are *Thalassiosira* sp. or *Chaetecoros* sp. The microalgae may be different diatoms and are cultivated photoautotrophically outdoors in open ponds for at least 14 days under filtered sunlight and at least 20% by weight of the fatty acids are EPA.

The use of this algae based oil overcomes the technical problems associated with the dwindling supplies of fish oil and/or Antarctic krill, which are now more difficult to harvest and obtain and use economically because these products are in high demand. A major difference between fish oils and algae based oils is their structure. Fish oils are storage lipids and are in the form of triacylglycerides. The algae based oils as lipids are a mixture of storage lipids and membrane lipids. The EPA and DHA present in algae based oils is mainly in the form of glycolipids and a small percentage is in the form of phospholipids. Glycolipids are primarily part of chloroplast membranes and phospholipids are part of cell membranes.

The '037 patent describes various methods for culturing microalgae photoautotrophically outdoors to produce EPA and DHA. One method used is filtering sunlight to reduce the light intensity on the photoautotrophic culture. Shade cloth or netting can be used for this purpose. It was determined that for most strains, the optimal solar intensity for growth, for maintaining a pure culture, and for omega-3 fatty acid accumulation was about 40,000 to 50,000 lux, approximately half of the 110,000 lux of full sunlight. Shade cloth or netting is suitable for filtering the sunlight to the desired intensity.

It is also possible to culture microalgae photoautotrophically outdoors and produce EPA and DHA by using small dilutions and a slow dilution rate of less than 40% per day, preferably less than 35% per day, more preferably from about 15% to about 30% per day. In other examples, the dilution rate is 15-40% per day or 15-35% per day, and in yet other examples, the dilution rate is 10-30%, 10-35%, or 10-40% per day. These smaller dilutions and lower dilution rates than are usually used help prevent contamination in outdoor photoautotrophic cultures. It also promotes thick culture growth that gives good DHA or EPA yield.

Another technique to successfully culture microalgae photoautotrophically outdoors and produce EPA and EPA/DHA is to harvest the microalgae in exponential phase rather than stationary phase. Harvesting in exponential phase reduces the risk of contamination in outdoor photoautotrophic cultures and has surprisingly been found to give a good yield of EPA and DHA. To drive fat accumulation in microbial cultures, the cultures are harvested in stationary phase because cells in the stationary phase tend to accumulate storage lipids. The '037 patent teaches that EPA and DHA accumulate in large amounts as membrane lipids in cultures harvested in the exponential phase. The membrane lipids containing EPA and DHA are predominantly phosphodiacylglycerides and glycodiacylglycerides, rather than the triaclyglycerides found in storage lipids. These cultures are harvested often when cell number is increasing at a rate at least 20% of the maximal rate, i.e., the maximal rate achieved at any stage during the outdoor photoautotrophic growth of the harvested culture. In specific examples, the cultures are harvested in exponential phase when cell number is increasing at a rate of at least 30%, at least 40%, or at least 50% of maximal rate. It is also possible to use recombinant DNA techniques.

The '037 patent includes several examples, which are referenced to the reader for description and teaching purposes.

EXAMPLE 1

The strain *Thalassiosira* sp. is a diatom and this strain used was isolated from Bay of Bengal, and it dominates during summer months. This example strain was isolated from seawater collected near Chemai, India, and the culture was maintained in open tubs. The particular strain was identified as *Thalassiosira weissflogii*, which is capable of growth at high temperatures (35-38° C.). The fatty acid profile was good even when the alga was grown at high temperature with 25-30% EPA (as a percentage of fatty acids).

Culturing: The lab cultures were maintained in tubs in an artificial seawater medium, under fluorescent lights (3000-4000 lux) and the temperature was maintained at 25° C. Initial expansion of the culture was done under laboratory condition in tubs. The dilution rate was 15% to 30% of the total culture volume per day. Once the volume was 40-50 liters, it was transferred to an outdoor pond. The outdoor ponds were covered with netting to control the light (40,000 to 50,000 lux). The dilution continued until the culture reached 100,000 liters volume. The culture was held in 500 square meter ponds at this time with a culture depth of 20 cm. The culture was stirred with a paddle wheel and CO2 was mixed to keep the culture pH neutral. When the EPA levels in the pond reached a desirable level (10-15 mg/lit), the whole pond was harvested by filtration. The filtered biomass was washed with saltwater (15 parts per thousand concentration) and then spray dried. The mode of culturing was batch mode. The EPA productivity was 2-3 mg/lit/day. The ponds can also be run continuously for several weeks by harvesting part of the culture, recycling the filtrate into the ponds and replenishing required nutrients.

EXAMPLE 2

The strain *Tetraselmis* sp. is in the division Chlorophyta and the class Prosinophyceae or Micromanadophyceae. This strain was obtained from the Central Marine Fisheries Research Institute, India. It was isolated from the local marine habitats in India. The culture was maintained in flasks in artificial seawater medium, and expanded as described for *Thalassiosira*. With culture outdoors in open ponds as described for *Thalassiosira*, the strain gave a good lipid yield (200-300 mg/liter) and an EPA content of 6-7% of fatty acids.

EXAMPLE 3

The strain *Chaetoceros* sp. is another diatom strain obtained from the Central Marine Fisheries Research Institute, India, and isolated from local marine habitats in India. *Chaetoceros* sp. was maintained in flasks and cultivated in outdoor ponds photoautotrophically as described in Example 1. It gave similar EPA productivity and EPA content as *Thalassiosira* as described in Example 1.

EXAMPLE 4

The strain *Isochrysis* sp. is in the Prymnesiophyta, class Prymnesiophyceae, order Isochrysidales. It was obtained from the Central Marine Fisheries Research Institute, India, and isolated from local marine habitats in India. It was maintained and grown as described in Example 1. It was expanded from laboratory culture to a 50,000 liter outdoor pond culture in 14-15 days with a dilution rate of 15-30% per day. The lipid content at harvest was 100-150 mg lipids/liter. The rate of lipid production was 25-50 mg/liter/day. DHA was 10-12% of total fatty acids.

EXAMPLE 5

Harvesting and Drying: The harvesting may be done by flocculation. The commonly used flocculants include Alum with polymer and FeCl3 with or without polymer and chitosan. The concentration of flocculent will depend on the cell number in the culture before harvest. The range may vary from 100 ppm to 500 ppm. Alternatively, harvesting is done by filtration using appropriate meshes. Removal of adhered chemicals (other than salt) is accomplished by washing the cells in low salinity water.

The harvested slurry is then taken for spray drying. The slurry is sometimes encapsulated to prevent oxidation. The concentration of encapsulating agent may vary from 0.1 to 1.0% on a dry weight basis. Modified starch is a suitable encapsulating agent. The spray dryer is usually an atomizer or nozzle type. The inlet temperature ranges from 160 to 190° C. and the outlet temperature ranges from 60 to 90° C. The spray dried powder is used immediately for extraction. If storage is required, the powder is packed in aluminum laminated pouches and sealed after displacing the air by nitrogen. The packed powder is stored at ambient temperature until further use.

EXAMPLE 6

Extraction of EPA/DHA is carried out using a wet slurry or dry powder and solvents, which include hexane, ethanol, methanol, acetone, ethyl acetate, isopropanol and cyclohexane and water, either alone or in combination of two solvents. The solvent to biomass ratio depends on the starting material. If it is a slurry, the ratio is 1:2 to 1:10. With a spray dried powder, on the other hand, the ratio is 1:4 to 1:30. The extraction is carried out in an extraction vessel under inert atmosphere, with temperature ranges from 25 to 60° C. and with time varying from one hour to 10 hours. Solvent addition is made one time or in parts based on the lipid level in the cells.

After extraction of crude lipid, the mixture is passed through a centrifuge or filtration system to remove the cell debris. The lipid in the filtrate is concentrated by removing the solvent by distillation, which is carried out under vacuum. The resulting product is a crude lipid extract, which contains approximately 10% omega-3 fatty acid (EPA/DHA). The extract can be used as it is or purified further to enrich the omega-3 fatty acids. Further purification may involve removal of unsaponifiables such as pigments, sterols and their esters.

The composition may have other uses besides improving blood lipid profiles and reducing low density lipoprotein (LDL) per-oxidation in humans or used with joint care treatment to reduce joint pain. Possible uses of the composition include use as a treatment for depression that may counter neurological disorders associated with depression. This could include treatment for a deficiency of neurotransmitters at post-synaptic receptor sites. The composition may be used to treat manic episodes in bipolar treatments and treat panic disorder and reduce the frequency and severity of panic attacks and the severity of agoraphobia. The composition may be used to treat Obsessive Compulsive Disorder (OCD) and malfunctioning neurotransmitters and serotonin receptors. The composition may also be used in the treatment of Alzheimer's Disease (AD) and reduce the presence of aluminosilicates at the core of senile plaque and diseased neurons. The composition may be used to treat aging disorders for cellular differentiation, proliferation and regeneration. It may also be used to treat age-related changes in mitochondrial function and age-related hearing loss. The composition may also possibly maintain metabolic activity and available energy by maintaining levels of phospholipids in normal cells and maintain membrane integrity and regulate enzyme activities and membrane transport processes through changes in membrane fluidity.

The composition may be beneficial for biological functions of essential fatty acids, including neural tissues such as the brain and retina and treat dementia-related diseases to increase mental function, memory, concentration and judgment and overcome the effects of Alzheimer's Disease. The composition may also be used to restore and preserve liver function and protect the liver against damage from alcoholism, pharmaceuticals, pollutant substances, viruses and other toxic influences that may damage cell membranes. It may possibly have antioxidant activity.

Additives may be used with the composition and pharmaceutical or nutraceutical formulations may be made by methods known in the art. For example, the composition may be formulated using one or more pharmaceutically or nutraceutically acceptable carriers. Thus, the composition may be formulated for oral administration. For oral administration, the pharmaceutical or nutraceutical compositions as compositions may take the form of, for example, tablets or capsules prepared by conventional techniques with pharmaceutically or nutraceutically acceptable excipients such as binding agents (e.g., pregelatinised maize starch, polyvinylpyrrolidone or hydroxypropyl methylcellulose); filters (e.g., lactose, microcrystalline cellulose or calcium phosphate); lubricants (e.g., magnesium stearate, talc or silica); disintegrants (e.g., potato starch or sodium starch glycollate); or wetting agents (e.g., sodium lauryl sulphate). The tablets may be coated by methods known in the art. Liquid preparations for oral administration may take the form of, for example, solutions, syrups or suspensions, or they may be presented as a dry product for use with water or another suitable vehicle before use. Such liquid preparations may be prepared by conventional techniques with pharmaceutically or nutraceutically acceptable additives such as suspending agents (e.g., sorbitol syrup, methyl cellulose or hydrogenated edible fats); emulsifying agents (e.g., lecithin or *acacia*); non-aqueous vehicles (e.g., almond oil, oily esters or ethyl alcohol); and preservatives (e.g., methyl or propyl p-hydroxybenzoates or sorbic acid).

When the composition is used as a nutraceutical, it can be in the form of foods, beverages, energy bars, sports drinks, supplements or other forms as known in the art. This composition is also useful in cosmetic preparations, e.g., moisturizing creams, sun-block products and other topical cosmetic products as known in the art.

The composition may possibly be used in the treatment or prevention of a variety of disease states including: liver disease; chronic hepatitis; steatosis; liver fibrosis; alcoholism; malnutrition; chronic parenteral nutrition; phospholipid deficiency; lipid peroxidation; disarrhythmia of cell regeneration; destabilization of cell membranes; coronary artery disease caused by hypercholesterolemia; high blood pressure; menopausal or post-menopausal conditions; cancer, e.g., skin cancer; hypertension; aging; benign prostatic hyperplasia; kidney disease; edema; skin diseases; gastrointestinal diseases; peripheral vascular system diseases (e.g. leg ulcers); pregnancy toxemia; and neurodegenerative and psychiatric diseases (e.g. Parkinson's, Alzheimer's, autism, attention deficit disorder, learning disorders, mood disorders, bipolar depression, multiple sclerosis, muscular dystrophy).

The composition may also be useful for targeting tumors and may be used in conjunction with radioisotopes for diagnosing central nervous system tumors. The composition may also be used to reduce local fat deposits and reducing visible cellulite. The composition may also be used in aesthetics such as breast enlargement by acting on the lobular tissue of the breast and by increasing hydration of the breast.

The composition may be used to treat and/or prevent cardiovascular diseases, arthritis, skin cancer, diabetes, premenstrual syndrome and transdermal transport enhancement. It may be used to decrease cholesterol in vivo and inhibit platelet adhesion and plaque formation and reduce vascular endothelial inflammation in a patient and offer hypertension prophylaxis. The composition may prevent oxidation of low-density lipoprotein and have an inhibitory effect on the secretion of VLDL possibly due to increased intracellular degradation of APO B-100. It may offer a post-myocardial infarction prophylaxis possibly because of its ability to decrease CIII apolipoprotein B, to decrease C3 non-apoliproprotein B lipoproteins and to increase antithrombin 3 levels. It may be suitable for prophylactic usage against cardiovascular disease in humans where it relates to coronary disease, hyperlipidemia, hypertension, ischemic disease such as relating to angina, myocardial infarction, cerebral ischemia, and shock without clinical or laboratory evidence of ischemia or arrhythmia.

The composition may be suitable to offer symptomatic relief for arthritis, Still's Disease, polyarticular or pauciarticular juvenile rheumatoid arthritis, rheumatoid arthritis, osteoarthritis, and may provide clinical improvement in decreasing the number of tender joints and analgesics consumed daily by decreasing the production of interleukin and interleukin-1 in human patients. The composition may also be used as a skin cancer prophylactic. It may have some retinal and anti-carcinogenic effects. It may enhance transdermal transportation as a substrate for dermatological topical therapeutic applications and may be used in dermatological treatments via creams, ointments, gels, lotions and oils and may be used in various therapeutic applications such as relating to anesthesic, corticosteroids, anti-inflammatory, antibiotic and ketolytic functions. It may also be used to enhance transdermal transportation as a substrate for dermatological topical cosmetic applications where cosmetic application relates to skin hydration, anti-wrinkle, caratolytics, peeling and mask via creams, ointments, gels, lotions or oils. The composition may be used to reduce the pain and mood changes associated with premenstrual syndrome in women.

The composition may be used to treat or prevent a cardiometabolic disorder/metabolic syndrome. The cardiometabolic disorder could be atherosclerosis, arteriosclerosis, coronary heart (carotid artery) disease (CHD or CAD), acute coronary syndrome (or ACS), valvular heart disease, aortic and mitral valve disorders, arrhythmia/atrial fibrillation, cardiomyopathy and heart failure, angina pectoris, acute myocardial infarction (or AMI), hypertension, orthostatic hypotension, shock, embolism (pulmonary and venous), endocarditis, diseases of arteries, the aorta and its branches, disorders of the peripheral vascular system (peripheral arterial disease or PAD), Kawasaki disease, congenital heart disease (cardiovascular defects) and stroke (cerebrovascular disease), dyslipidemia, hypertriglyceridemia, hypertension, heart failure, cardiac arrhythmias, low HDL levels, high LDL levels, stable angina, coronary heart disease, acute myocardial infarction, secondary prevention of myocardial infarction, cardiomyopathy, endocarditis, type 2 diabetes, insulin resistance, impaired glucose tolerance, hypercholesterolemia, stroke, hyperlipidemia, hyperlipoproteinemia, chronic kidney disease, intermittent claudication, hyperphosphatemia, omega-3 deficiency, phospholipid deficiency, carotid atherosclerosis, peripheral arterial disease, diabetic nephropathy, hypercholesterolemia in HIV infection, acute coronary syndrome (ACS), non-alcoholic fatty liver disease/non-alcoholic steatohepatitis (NAFLD/NASH), arterial occlusive diseases, cerebral atherosclerosis, arteriosclerosis, cerebrovascular disorders, myocardial ischemia, coagulopathies leading to thrombus formation in a vessel and diabetic autonomic neuropathy.

The composition may also be used to treat, prevent or improve cognition and/or a cognitive disease, disorder or impairment (memory, concentration, learning (deficit)), or of treating or preventing neurodegenerative disorders. The cognitive disease, disorder or impairment could be Attention Deficit Disorder (ADD), Attention Deficit Hyperactivity Disorder (ADHD), autism/autism spectrum disorder (ASD), (dyslexia, age-associated memory impairment and learning disorders, amnesia, mild cognitive impairment, cognitively impaired non-demented, pre-Alzheimer's disease, Alzheimer's disease, epilepsy, Pick's disease, Huntington's disease, Parkinson disease, Lou Gehrig's disease, pre-dementia syndrome, Lewy body dementia dementia, dentatorubropallidoluysian atrophy, Freidreich's ataxia, multiple system atrophy, types 1, 2, 3, 6, 7 spinocerebellar ataxia, amyotrophic lateral sclerosis, familial spastic paraparesis, spinal muscular atrophy, spinal and bulbar muscular atrophy, age-related cognitive decline, cognitive deterioration, moderate mental impairment, mental deterioration as a result of ageing, conditions that influence the intensity of brain waves and/or brain glucose utilization, stress, anxiety, concentration and attention impairment, mood deterioration, general cognitive and mental well being, neurodevelopmental, neurodegenerative disorders, hormonal disorders, neurological imbalance or any combinations thereof. The cognitive disorder may be memory impairment.

The composition may be used to inhibit, prevent or treat inflammation or an inflammatory disease. The inflammation or inflammatory disease may be due to organ transplant rejection; reoxygenation injury resulting from organ transplantation (see Grupp et al., J. Mol. Cell, Cardiol. 31: 297-303 (1999)) including, but not limited to, transplantation of the following organs: heart, lung, liver and kidney; chronic inflammatory diseases of the joints, including arthritis, rheumatoid arthritis, osteoarthritis and bone diseases associated with increased bone resorption; inflammatory bowel diseases (IBD) such as ileitis, ulcerative colitis (UC), Barrett's syndrome, and Crohn's disease (CD); inflammatory lung diseases such as asthma, acute respiratory distress syndrome (ARDS), and chronic obstructive pulmonary disease (COPD); inflammatory diseases of the eye including corneal dystrophy, trachoma, onchocerciasis, uveitis, sympathetic ophthalmitis and endophthalmitis; chronic inflammatory diseases of the gum, including gingivitis and periodontitis; inflammatory diseases of the kidney including uremic complications, glomerulonephritis and nephrosis; inflammatory diseases of the skin including sclerodermatitis, psoriasis and eczema; inflammatory diseases of the central nervous system, including chronic demyelinating diseases of the nervous system, multiple sclerosis, AIDS-related neurodegeneration and Alzheimer's disease, infectious meningitis, encephalomyelitis, Parkinson's disease, Huntington's disease, epilepsy, amyotrophic lateral sclerosis and viral or autoimmune encephalitis, preeclampsia; chronic liver failure, brain and spinal cord trauma, and cancer. The inflammatory disease may also be a systemic inflammation of the body, exemplified by gram-positive or gram negative shock, hemorrhagic or anaphylactic shock, or shock induced by cancer chemotherapy in response to pro-inflammatory cytokines, e.g., shock associated with pro-inflammatory cytokines. Such shock can be induced, e.g., by a chemotherapeutic agent that is administered as a treatment for cancer. Other disorders include depression, obesity, allergic diseases, acute cardiovascular events, muscle wasting diseases, and cancer cachexia. Also, inflammation that results from surgery and trauma may possibly be treated.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. A method to treat low density lipoprotein (LDL) peroxidation in humans by administering a therapeutic amount of a dietary supplement composition comprising 0.5 to 12 mg of astaxanthin derived from *Haematococcus pluvialis* (Hp), and 50 to 500 mg of a lipid selected from the group consisting of a phospholipid, glycolipid, and sphingolipid, wherein the astaxanthin is 0.1 to 15 percent by weight of the lipid selected from the group consisting of a phospholipid, glycolipid and sphingolipid, and wherein the composition is formulated into an oral dosage form as a single dosage capsule.

2. The method according to claim 1, wherein the composition being administered further comprises a pharmaceutical or food grade diluent.

3. The method according to claim 1, wherein the phospholipid is selected from the group consisting of Phosphatidylcholine, Phosphatidylethanolamine, Phosphatidylserine, Phosphatidylinositol, Phosphatidic acid, Lysophosphatidylcholine Lysophosphatidylethanolamine, and Lysophosphatidylserine.

4. The method according to claim 1, wherein the phospholipid comprises at least one of a plant, algae and animal source derivative.

5. The method according to claim 1, wherein the composition has the astaxanthin dispersed into the selected lipid under high shear conditions.

6. A method to treat low density lipoprotein (LDL) peroxidation in humans by administering a therapeutic amount of a dietary supplement composition comprising 0.5 to 12 mg of astaxanthin derived from *Haematococcus pluvialis* (Hp) and 50 to 500 mg of a phospholipid, wherein the astaxanthin is 0.1 to 15 percent by weight of the phospholipid, and wherein the composition is formulated into an oral dosage form as a single dosage capsule.

7. The method according to claim 6, wherein the composition being administered further comprises a pharmaceutical or food grade diluent.

8. The method according to claim 6, wherein the phospholipid is selected from the group consisting of Phosphatidylcholine, Phosphatidylethanolamine, Phosphatidylserine, Phosphatidylinositol, Phosphatidic acid, Lysophosphatidylcholine Lysophosphatidylethanolamine and Lysophosphatidylserine.

9. The method according to claim 6, wherein the phospholipid comprises at least one of a plant, algae or animal source derivative.

10. The method according to claim 6, wherein the composition has the astaxanthin dispersed into the selected lipid under high shear conditions.

* * * * *